US010303986B2

(12) United States Patent
Najarian et al.

(10) Patent No.: US 10,303,986 B2
(45) Date of Patent: May 28, 2019

(54) AUTOMATED MEASUREMENT OF BRAIN INJURY INDICES USING BRAIN CT IMAGES, INJURY DATA, AND MACHINE LEARNING

(76) Inventors: Kayvan Najarian, Glen Allen, VA (US); Wenan Chen, Richmond, VA (US); Kevin R. Ward, Glen Allen, VA (US)

( * ) Notice: Subject to any disclaimer, the term of this patent is extended or adjusted under 35 U.S.C. 154(b) by 377 days.

(21) Appl. No.: 13/383,351

(22) PCT Filed: Mar. 17, 2010

(86) PCT No.: PCT/US2010/027584
§ 371 (c)(1),
(2), (4) Date: Jan. 10, 2012

(87) PCT Pub. No.: WO2010/117573
PCT Pub. Date: Oct. 14, 2010

(65) Prior Publication Data
US 2012/0184840 A1 Jul. 19, 2012

Related U.S. Application Data

(60) Provisional application No. 61/167,284, filed on Apr. 7, 2009.

(51) Int. Cl.
*A61B 5/00* (2006.01)
*G06K 9/62* (2006.01)
(Continued)

(52) U.S. Cl.
CPC ............ *G06K 9/629* (2013.01); *G06T 7/0012* (2013.01); *G06T 7/42* (2017.01); *G06T 7/68* (2017.01);
(Continued)

(58) Field of Classification Search
None
See application file for complete search history.

(56) References Cited

U.S. PATENT DOCUMENTS 6,591,004 B1 * 7/2003 VanEssen et al. ............ 600/410
8,199,985 B2 * 6/2012 Jakobsson et al. ........... 382/128
(Continued)

FOREIGN PATENT DOCUMENTS

WO    WO 2007/110420 A2 * 10/2007    ............... G06T 5/00

OTHER PUBLICATIONS

Hiler et al., "Predictive value of initial computerized tomography scan intracranial pressure, and state of autoregulation in patients with traumatic brain injury" J. Neurosurg 104: 731-737, May 2006.*
(Continued)

*Primary Examiner* — Joel F Brutus
(74) *Attorney, Agent, or Firm* — Marshall, Gerstein & Borun LLP

(57) ABSTRACT

A decision-support system and computer implemented method automatically measures the midline shift in a patient's brain using Computed Tomography (CT) images. The decision-support system and computer implemented method applies machine learning methods to features extracted from multiple sources, including midline shift, blood amount, texture pattern and other injury data, to provide a physician an estimate of intracranial pressure (ICP) levels. A hierarchical segmentation method, based on Gaussian Mixture Model (GMM), is used. In this approach, first an Magnetic Resonance Image (MRI) ventricle template, as prior knowledge, is used to estimate the region for each ventricle. Then, by matching the ventricle shape in CT images to the MRI ventricle template set, the corresponding MRI slice is selected. From the shape matching result, the
(Continued)

feature points for midline estimation in CT slices, such as the center edge points of the lateral ventricles, are detected. The amount of shift, along with other information such as brain tissue texture features, volume of blood accumulated in the brain, patient demographics, injury information, and features extracted from physiological signals, are used to train a machine learning method to predict a variety of important clinical factors, such as intracranial pressure (ICP), likelihood of success a particular treatment, and the need and/or dosage of particular drugs.

30 Claims, 14 Drawing Sheets

(51) Int. Cl.
  *G06T 7/00* (2017.01)
  *G06T 7/42* (2017.01)
  *G06T 7/68* (2017.01)
  *G06F 19/00* (2018.01)
  *G16H 50/20* (2018.01)

(52) U.S. Cl.
  CPC ...... *G06F 19/321* (2013.01); *G06K 2209/055* (2013.01); *G06T 2207/10081* (2013.01); *G06T 2207/20056* (2013.01); *G06T 2207/20064* (2013.01); *G06T 2207/30016* (2013.01); *G16H 50/20* (2018.01); *Y02A 90/26* (2018.01)

(56) References Cited

U.S. PATENT DOCUMENTS

| | | | |
|---|---|---|---|
| 2005/0283070 A1* | 12/2005 | Imielinska et al. | 600/425 |
| 2009/0292198 A1* | 11/2009 | Kleiven et al. | 600/416 |
| 2010/0260396 A1* | 10/2010 | Brandt | G06K 9/4671 382/131 |
| 2011/0026798 A1* | 2/2011 | Madabhushi | G01R 33/56 382/131 |

OTHER PUBLICATIONS

Yin et al., "Medical Image Categorization Based on Gaussian Mixture Model," 2008 International Conference on BioMedical Engineering and Informatics on May 27-30, 2008, pp. 128-131, 2008.*

Ji et al., "A comparative analysis of multi-level computer-assisted decision making systems for traumatic injuries," BMC Medical Informatics and Decision Making, 9:2, pp. 1-17, 2009.*

Marshall et al., "A new classification of head injury based on computerized tomography," J. Neurosurg., vol. 75, pp. S14-S20 (Nov. 1991).*

Chen et al., "Automated Segmentation of Lateral Ventricles in Brain CT Images," in Bioinformatics and Biomedicine Workshops 2008, IEEE International Conference Dec. 2008, pp. 48-55.*

Belongie et al., Shape matching and object recognition using shape contexts, IEEE Trans. on Pattern Analysis and Machine Intelligence, 24(25):509-21 (2002).

Dempster et al., Maximum Likelihood from incomplete data via the $EM$ algorithm, J. Royal Stat. Soc. B, 39(1):1-38 (1977).

Greenspan et al., Constrained Gaussian mixture model framework for automatic segmentation of MR brain images, IEEE Trans. Med. Imaging, 25(9):1233-45 (2006).

Kingsbury, Complex wavelets for shift invariant analysis and filtering of signals, J. Appl. Comput. Harmonic Anal., 10(3):234-53 (2001).

Liao et al., A simple genetic algorithm for tracing the deformed midline on a single slice of brain CT using quadratic Bezier curves, Data Mining Workshops, 2006. ICDM Workshops 2006. Sixth IEEE International Conference on Data Mining, pp. 463-467 (2006).

Manthalkar et al., Rotation and scale invariant texture features using discrete wavelet packet transform, Pattern Recognition Lett., 24(14):2455-62 (2003).

Najaran et al.,Biomedical Signal and Image Processing, CRC Press (Dec. 21, 2005).

Robnik-Sikonja et al., An adaptation of relief for attribute estimation in regression, Proceedings of the Fourteenth International Conference on Machine Learning, pp. 296-304 (1997).

Tang, Texture information in run-length matrices, IEEE Trans. Image Process., 7(11):1602-9 (1998).

* cited by examiner

AUTOMATED MEASUREMENT OF BRAIN INJURY INDICES USING BRAIN CT IMAGES, INJURY DATA, AND MACHINE LEARNING

CROSS-REFERENCE TO RELATED APPLICATIONS

This application is a U.S. National Phase of International Application No. PCT/US10/27584, filed Mar. 17, 2010, which claims the priority benefit under 35 U.S.C. § 119(e) of U.S. Provisional Application No. 61/167,284, filed Apr. 7, 2009, the disclosures of all of which are incorporated herein by reference in their entirety.

BACKGROUND OF THE INVENTION

Field of the Invention

The present invention generally relates to a decision-support system and computer implemented method to automatically measure the midline shift using Computed Tomography (CT) images and, more particularly, to a decision-support system and computer implemented method that applies machine learning methods to features extracted from multiple sources, including midline shift, blood amount, texture pattern and other injury data, to provide a physician an estimate of intracranial pressure (ICP) levels.

Background Description

It is estimated that every year, 1.5 million people in the United States sustain traumatic brain injuries (TBI). Over 50,000 of these patients will not survive, and many others will be left permanently disabled. The severity of TBI is known to be accompanied by an increase in intracranial pressure (ICP), as the presence of hematomas compresses the brain tissue.

Severe ICP can be fatal, and so must be monitored. This typically requires cranial trepanation, a risky procedure for the patient. However, some signs of increased ICP are visible on medical scans. For example, midline shift usually happens due to some locally increased ICP and can be captured from the brain Computed Tomography (CT) scans. These images provide an opportunity for non-invasive monitoring of ICP which can be used as a pre-screening step for cranial trepanation. Since the speed of diagnosis is vital, CT imaging is still the gold standard for initial TBI assessment. CT scanning is usually capable of clearly revealing any severe abnormalities such as fractures or hematomas.

While CT scans are commonly used for detection of gross injuries in the brain, midline shift of the brain is usually measured by simple visual inspection by physicians. Inaccurate or inconsistent CT image reading is often associated with the nature of the human visual system and the complex structure of the brain. Small midline shifts are elusive but are often invaluable for assessment of brain injury, in particular before a patient's condition becomes more severe. Failure to detect these small changes in brain alignment can result in underestimation of the severity of injury leading to inaction on the part of healthcare providers. This in turn may result in suboptimal patient outcomes.

SUMMARY OF THE INVENTION

An embodiment of the invention provides novel image processing techniques and computer vision methods, as well as expert clinical knowledge, combined to quantitively mimic how physicians read and interpret CT scans in order to more accurately detect shifting of brain tissue, i.e., "midline shift", or a significant change in the size of lateral ventricles.

According to an embodiment of the invention, when coupled with additional automated measures such as brain tissue texture, quantification of hematoma volume and imputation of pertinent demographic and injury data, machine learning computational techniques are applied to predict other important diagnostic information such as intracranial pressure (ICP).

The method implemented first detects the ideal midline based on anatomical features in the brain, bones, and tissues. The ideal midline is an imaginary midline if there were no injuries. Image processing techniques are designed to detect the protrusion in the anterior part of the bone and the falx cerebri in the posterior region of the brain tissue. These anatomical features are exactly the ones inspected by physicians in visual inspection of CT scans. The difficulty of detecting these anatomical features is that there are many other brain structures in the CT images which may interfere or mislead this process. As such, prior knowledge on anatomical structure is used to address this issue. Specifically, prior knowledge is used to approximately identify the regions of these structures and then refine the search using advanced signal processing method. This approach provides both high speed and high accuracy.

The next step is to segment out the ventricles from merest of the brain. Since there is no obvious midline across the center of die brain, ventricle system deformation is analyzed to obtain the midline deformation in these regions. Having the result of the ventricle segmentation, the actual midline, i.e., the midline after injury, can be estimated. A hierarchical segmentation method, based on Gaussian Mixture Model, is used for this step. In this approach, first a Magnetic Resonance Image (MRI) ventricle template, as prior knowledge, is used to estimate the region for each ventricle. Then, by matching the ventricle shape in CT images to the MRI ventricle template set, the corresponding MRI slice is selected. From the shape matching result, the feature points for midline estimation in CT slices, such as the center edge points of the lateral ventricles, are detected.

Once the segmentation process is completed, the actual midline is estimated based on these feature points. Using shape match to estimate the actual midline provides a robust and accurate process, which successfully deals a very wide range of pathological cases. After both ideal midline and actual midline are detected, the shift or deformation can be calculated. This shift indicates the midline deformation around the ventricle system.

Finally, the amount of shift, along with other information such as brain tissue texture features, volume of blood accumulated in the brain, patient demographics, injury information, and features extracted from physiological signals, are used to train a machine learning method to predict a variety of important clinical factors, such as intracranial pressure (ICP).

The invention provides accurate detection of ideal midline, the use of both anatomical features and spatial templates derived from MRI images to identify ventricles from pathological CT images, and a novel multiple regions shape matching algorithm which provides a very robust actual midline estimation method to deal with diverse ventricle shapes. The invention provides a practical, accurate, automated method for measurement of midline shift from CT images, accurate detection of ventricles from CT image, accurate and non-invasive estimation of ICP, accurate non-invasive screening/diagnostics as well as treatment planning. The application of the technique according to the invention can help physicians avoid time consuming, invasive, risky, and costly alternatives.

This technology can be used to determine which patients will require more aggressive monitoring and treatment options. For example, systems implementing the invention can be used in emergency department and intensive care units to help measure the midline shift as well as the ICP automatically. Once a threshold is reached, actions can be taken by physicians. The technology implementing the invention relates the midline shift to the Intracranial Pressure (ICP) and provides an estimation of ICP without invasive operations. Moreover, the technology and approach would benefit other brain injuries such as stroke and infection.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

In clinic settings, the midline shift is widely accepted as an indicator of elevated intracranial pressure (ICP). However, the relation applies only when the midline shift is obvious enough which indicates very high ICP and thus is usually too late for timely treatment. An aim of the present invention is to reveal the relation of ICP with all levels of midline shift as well as other information, such as brain tissue texture in CT images, hematoma volume and pertinent demographic and injury data. The final result is an accurate prediction of ICP to assist medical decisions.

An embodiment of the invention is described in terms of a decision-support system on which the methods of the invention may be implemented. The system is composed of various signal processing components, imaging processing components, databases and computational interfaces that one of ordinary skill in the computational and signal processing arts will be familiar with. The methods of the invention are described with reference to flowcharts which illustrate the logic of the processes implemented. The flowcharts and the accompanying descriptions are sufficient for one of ordinary skill in the computer programming, signal processing and image processing arts to prepare the necessary code to implement the embodiment of the invention.

Figure 1:
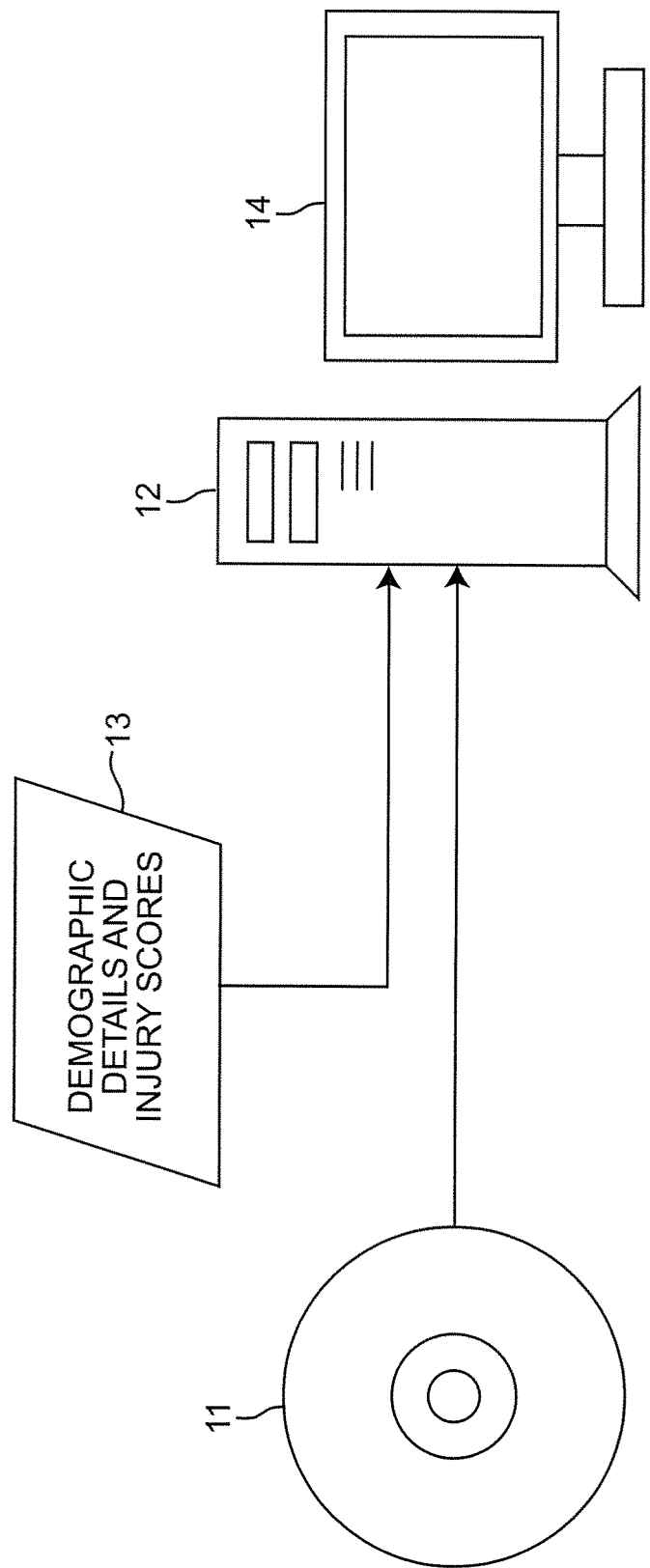
FIG. 1 is a block diagram of a system on which an embodiment of the invention can be implemented.

Referring to the drawings, and more particularly to FIG. 1, there is shown a decision-support system on which the embodiment of the invention may be implemented. Computed tomography (CT) images are generated of the patient's brain by a CT imaging machine 11. The CT image slices are input to a computer or data processing system 12 which is programmed to perform signal processing and image processing described in more detail with reference to the flowcharts which follow. The computer 12 also receives as inputs 13 demographic details and injury scores of the patient. The demographic details and injury scores may be input directly to the computer or data processing system 12 by means of user interface, such as a keyboard, or from a network where that information has been previously entered and stored. The computer 12 performs computations which measure the midline shift as well as the ICP automatically. The results of these computations are displayed on display 14 and provide an indication of ICP severity classification to assist a physician in making therapeutic decisions concerning the patient.

Figure 2:
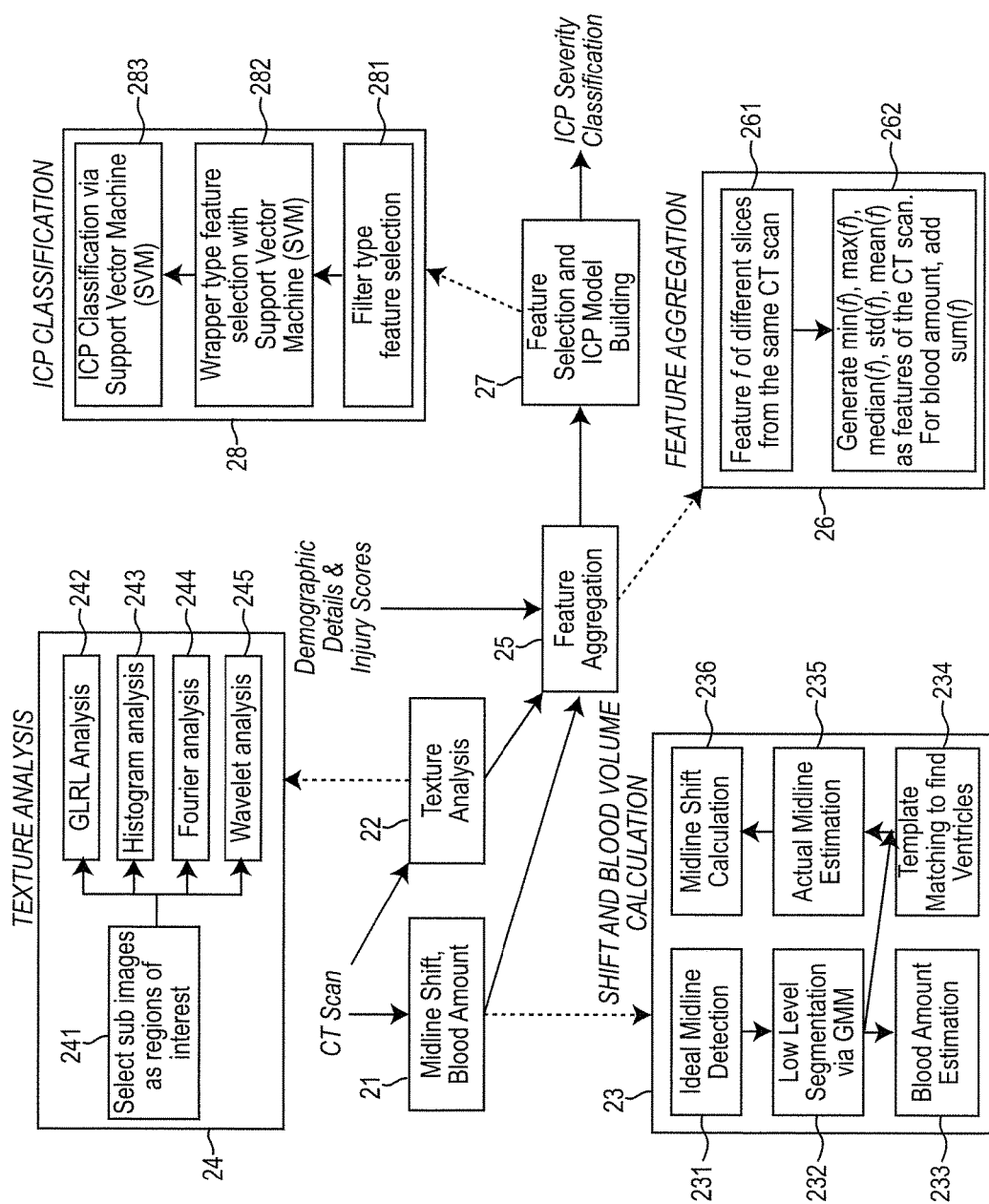
FIG. 2 is a block diagram illustrating the various components of the embodiment implemented on the system of FIG. 1.

The embodiment of the invention implemented on the decision-support system shown in FIG. 1 is illustrated in FIG. 2 and provides an ICP prediction using standard axial Computed Tomography (CT) images of the brain collected from the patient to be used as a screening procedure prior to invasive monitoring. ICP estimation can be repeated with every new scan taken, providing an updated estimate each time. The system is also able to be dynamically updated by generating new predictive models as more patient data becomes available. The CT scan is input to two subsystems of the system: the midline shift, blood amount subsystem 21 and the texture analysis subsystem 22. As illustrated, the process of subsystem 21 is briefly illustrated at 23. This process begins with the ideal midline detection step 231. Next, at step 232, low level segmentation is performed via Gaussian Mixture Model (GMM). At step 233, blood amount estimation is computed, and at step 234, template matching is performed to find ventricles. Then, in step 235, an estimate of actual midline is calculated. Finally, in step 236, the midline shift is calculated.

The process of subsystem 22 is briefly illustrated at 24. The first step 241 is to select sub-images as regions of interest. Then, in parallel, a Grey Level Run Length (GLRL) analysis is made at step 242, a histogram analysis is made at step 243, a Fourier analysis is made at step 244, and a wavelet analysis is made at 245.

The outputs of the midline shift subsystem 21 and the texture analysis subsystem 22 are input to a feature aggregation subsystem 25, which also receives as input demographic details and injury scores. As previously mentioned, the demographic details and injury scores may be input directly to the computer or data processing system 12 by means of user interface, such as a keyboard, or from a network where that information has been previously entered and stored. The process of the feature aggregation subsystem 25 is briefly illustrated at 26. The first step 261 is to determine feature f of different slices from the same CT scan. Then, in step 262, the min(f), max(f), median (f), std(f), and mean(f) are generated as features of the CT scan. For blood amount, sum(f) is added.

The output of the feature aggregation subsystem 25 is input to the feature selection and ICP model building subsystem 27. The process of the feature selection and ICP model building subsystem 27 is briefly illustrated at 28. The first step 281 is filter type feature selection. Next, in step 282, wrapper type feature selection with Support Vector Machine (SVM) is performed. Finally, in step 283, ICP classification via Support Vector Machine (SVM) is performed. The output of the feature selection and ICP model building subsystem is an ICP severity classification.

Figure 3:
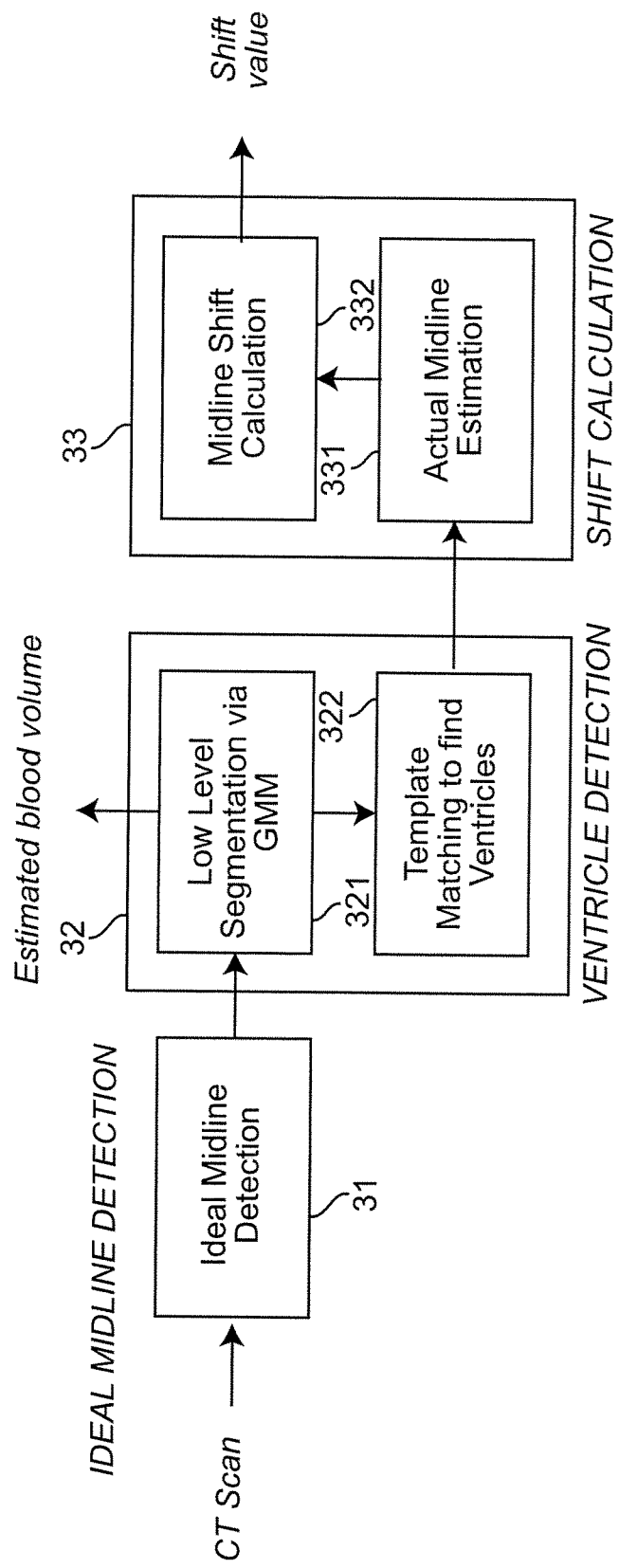
FIG. 3 is a flowchart illustrating the logic implemented by the midline shift detection component of the embodiment shown in FIG. 2.

Having described the overview of the system, each of the several subsystems of the system will now be described in greater detail. FIG. 3 presents a flowchart describing the operation of the midline shift and blood amount detection subsystem 23 shown in FIG. 2. This subsystem analyzes the full axial (top-down) Computed Tomography (CT) scan set of images and returns a quantitative estimate of any midline shift that has occurred. Due to the rigid structure of the skull, edema (swelling) of the brain caused by injury or disease can lead to shift and compression of soft tissue, which is associated with an elevated level of ICP. The degree of shift can be calculated as the difference between the "ideal midline" of the brain and the "actual midline" of the brain, as detected in the slices of an axial CT scan. In both these terms, "midline" refers to a line running from the front to the back of the skull in an axial view; over multiple slices, this extends into a plane dividing the left arid right hemispheres of the brain.

The ideal midline, i.e., what the midline would be if the patient were healthy, is detected at step 31 using a novel combination of skull symmetry and knowledge of anatomical structures. The actual midline is detected at step 32 by locating the ventricles in the slice images. These are displaced along with the other soft brain tissues in cases of high ICP, but are easier to detect due to their darker grayscale values in a CT image. The "actual midline" of the brain is the vertical line that is approximately halfway between the left and right ventricles. The first step 321 in the process is low level segmentation via Gaussian Mixture Model (GMM). One of the outputs of this process is estimated blood volume. Another output is provided to step 322 in which template matching is performed to find the ventricles. At step 33, the shift calculation is performed. The first step 331 is to make an estimation of the actual midline. Then, in step 332, the midline shift calculation is made. The output is the shift value.

Figure 4:
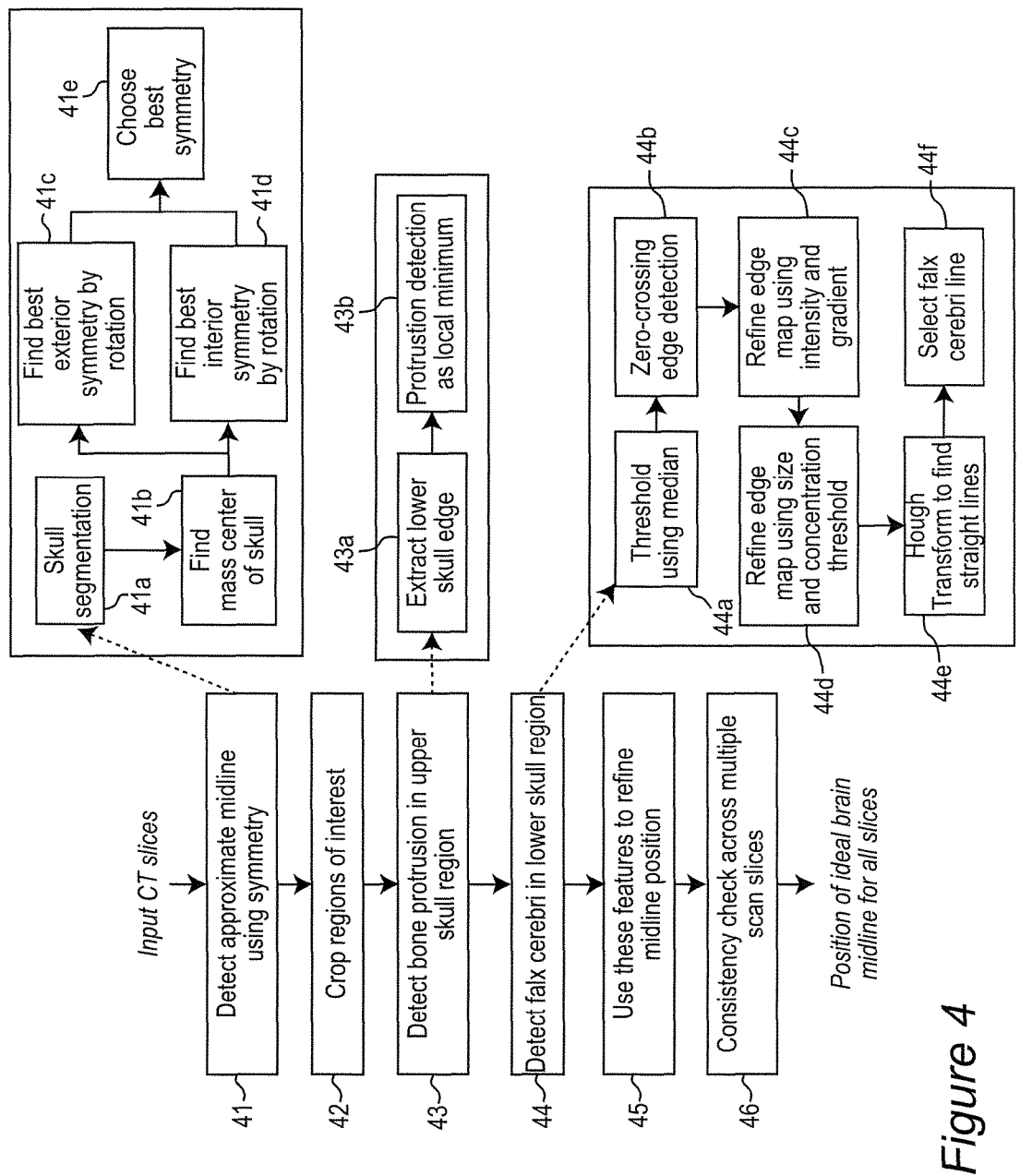
FIG. 4 is a flowchart illustrating in more detail the logic implemented by the midline detection component shown in FIG. 3.

FIG. 4 shows in more detail the process of the ideal midline detection component 31 shown in FIG. 3. This stage of the system detects the ideal midline of the brain via analysis of an axial CT brain scan (as a sequence of slice images).

Figure 5:
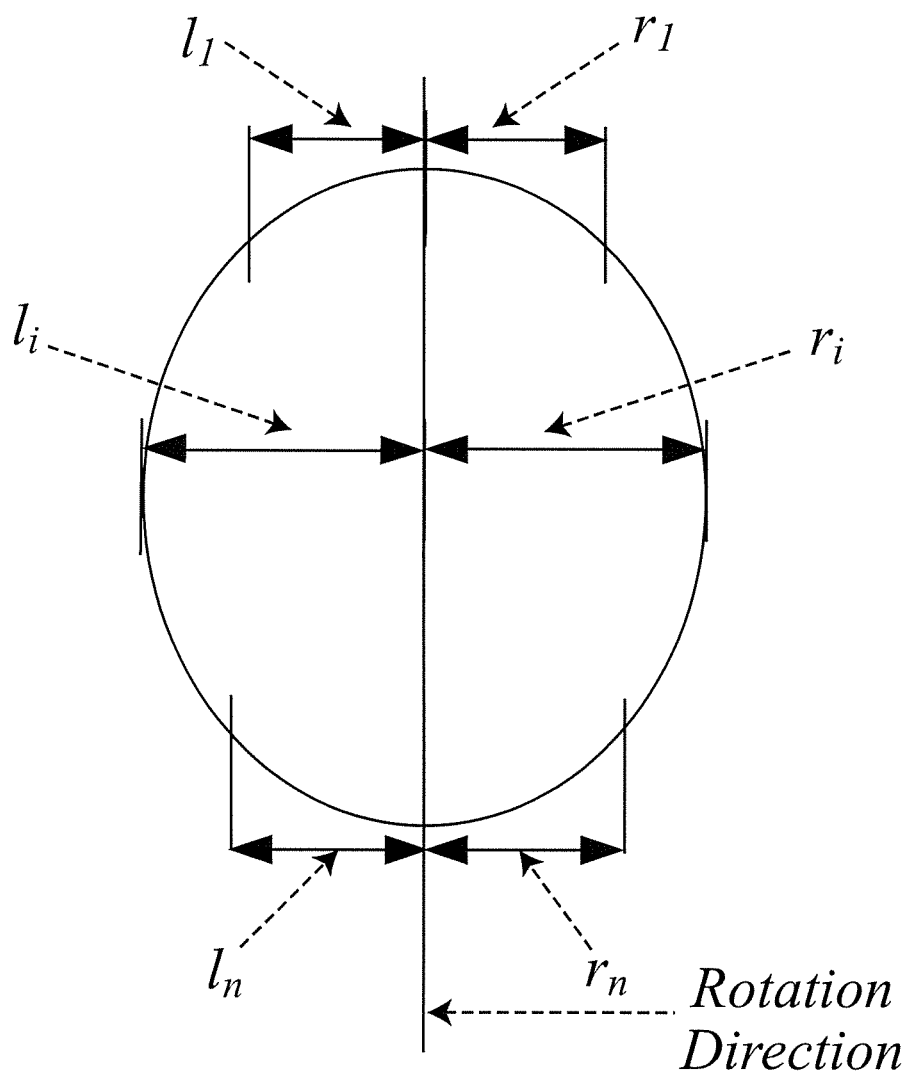
FIG. 5 is a graphical illustration showing how the symmetry measure is calculated by the midline detection component.

The first step 41 is to detect approximate midline using symmetry. An exhaustive rotation angle search around the mass center of the skull is used to find a dividing line that maximizes the symmetry of the two resulting halves. This is taken to be the approximate ideal midline. The sub-steps from step 41 explain this process in more detail. At steps 41$a$ and 41$b$, the skull is segmented from the CT slice and the mass center is found. First, a bone mask image is created by applying binary thresholding to the CT slice. This sets all pixels below a predefined grey-level threshold to binary 0, and those above the threshold to binary 1. Bone matter appears as very close to white in a CT scan, so if the threshold is set close to the maximum possible, the resulting binary image will contain only the structure of the skull wall. The mass center of the skull is calculated as the centroid of the skull object. At steps 41$c$ and 41$d$, the best interior and exterior symmetry is found by rotation. The slice image is gradually rotated around the center of mass of the skull, and symmetry measurements are made at each step. Symmetry is defined here as the sum of the symmetry of each row in the image after rotation. The row symmetry is defined as the difference in distance between each side of the skull edge and the current approximate midline. For each rotation direction $\theta_j$, the symmetry cost $S_j$ is defined as:

$$S_j = \sum_{i=1}^{n} |l_i - r_i| \quad (1)$$

where n is the number of rows image covering the skull, and measures $l_i$ and $r_i$ are as depicted in FIG. 5.

This method shares similarities with the method used in "A simple genetic algorithm for tracing the deformed midline on a single slice of brain ct using quadratic bezier curves" (C.-C. Liao, F. Xiao, J.-M. Wong, and I.-J. Chiang, *ICDMW '06: Proceedings of the Sixth IEEE International Conference on Data Mining—Workshops*, pp. 463-467, Washington, D.C., 2006, IEEE Computer Society); however, the method implemented by this embodiment of the invention incorporates both the interior and exterior edge of skull into the assessment for improved performance. Using the exterior edge can prove problematic if the skull wall is not of uniform thickness; this does not usually affect the interior edge. However, in some cases, the presence of shape irregularities inside the skull (especially in the lower region of the brain) make the exterior edge a better choice for evaluating symmetry. Consequently, both the interior and exterior edges are tested at each rotation step.

At step 41$e$, the best symmetry chosen. The rotation step with the best symmetry measurement (i.e., the lower symmetric cost) is chosen for each edge. These may be different steps. The two measurements are compared and the edge with final lowest cost is used.

Step 41 returns the approximate position of the ideal midline. However, symmetry provides only a coarse estimation, which must be refined for an accurate final shift calculation. The next few steps attempt to detect two anatomical structures at the anterior and posterior of the skull, which are then used to construct a more accurate ideal midline. These are the falx cerebri and the anterior bone protrusion. To isolate the areas where these structures are likely to appear, the regions of interest, two windows are extracted in step 42 from the CT slice image at either end of the approximate ideal midline to crop the regions of interest.

Figure 6:
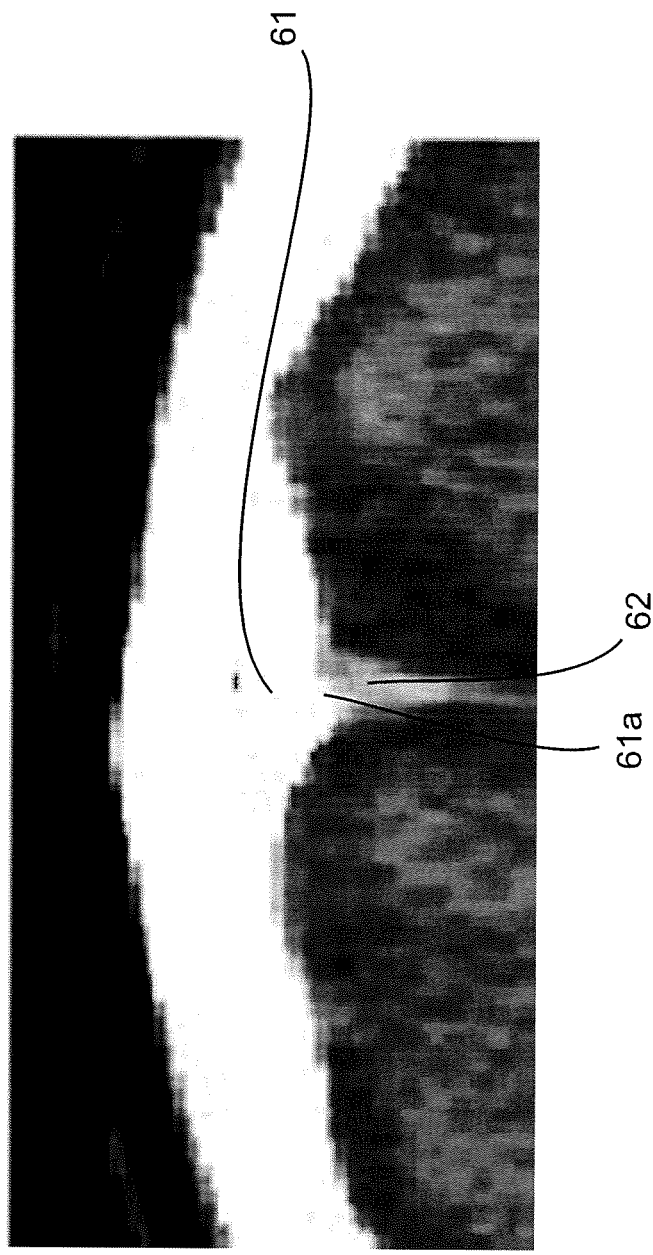
FIG. 6 is a microphotograph showing a magnified detail part of the anterior protrusion.
Figure 7:
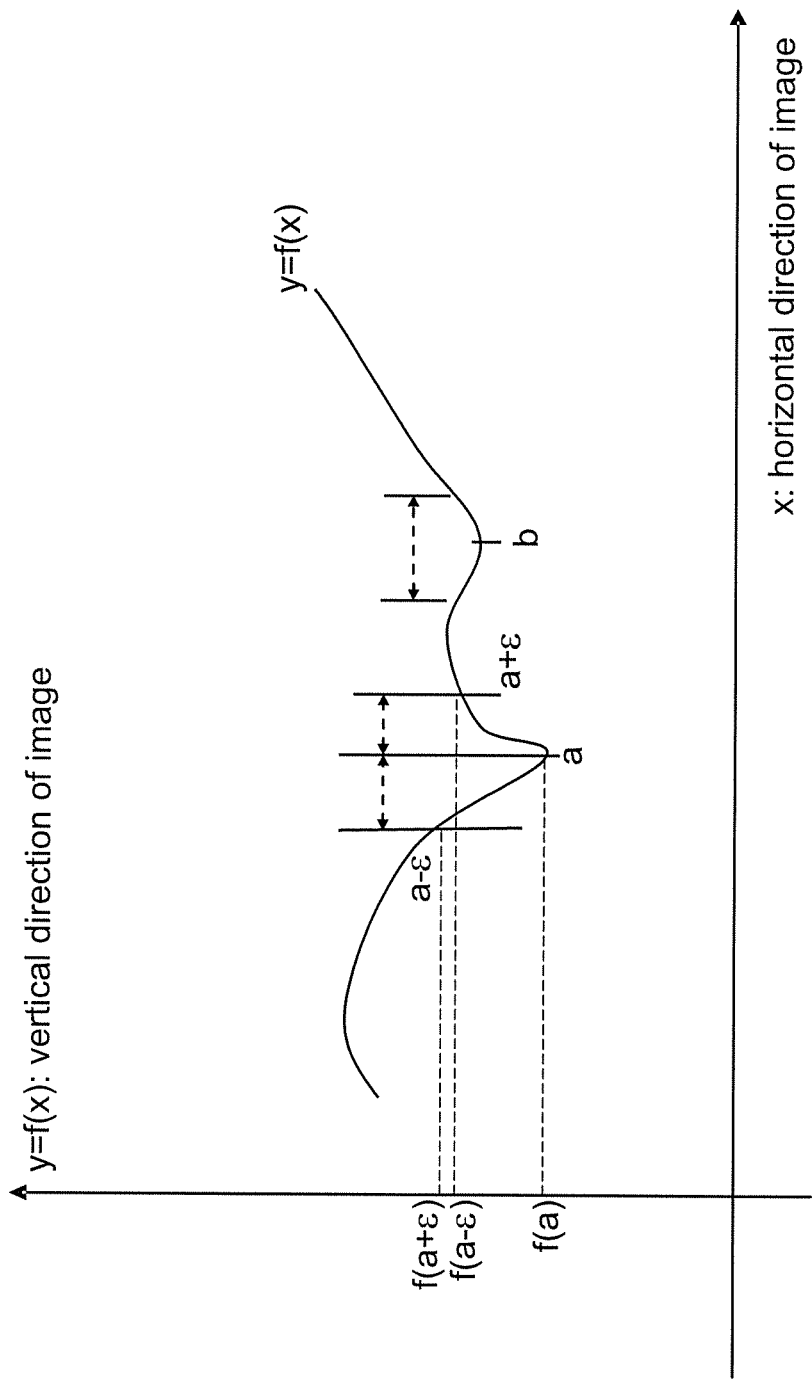
FIG. 7 is a graph showing the skull wall as a one dimensional (1D) graphed function.

At step 43, bone protrusion in upper skull region is detected. First, the window is likely to contain the anterior bone protrusion 61, as shown in FIG. 6. It can be seen in FIG. 6 that the skull wall curves down to a local minimum point 61*a* at the anterior edge of the falx cerebri line 62 (which divides the brain into separate hemispheres). This protrusion 61 can be used as a starting point for ideal midline detection. In step 43*a*, the lower skull edge is extracted. First, the lower skull edge is extracted from the image region, again using a binary threshold as described above with reference to step 41*a*. At step 43*b*, the protrusion is detected as local minimum. If one views the inside edge of the skull wall as a curve on the image plane, then the curve can be modeled as a one dimensional (1D) function. Detection of the protrusion point 61 (shown in FIG. 6) becomes a matter of sampling this function and finding the minimum. However, there are often multiple local minima along the curve due to image noise and skull wall irregularities. FIG. 7 graphically shows the curve of a typical skull wall in the region of interest. The difference between point a, the true minimum, and point b, a small protrusion, is the size of the slope around them. This is captured by calculating the derivative over a larger neighborhood; typically 10 to 15 pixels. Obtaining a derivative of exactly zero, the usual indicator of a function minimum, may not be possible, so the algorithm instead searches for transition points between a negative and positive derivative. To avoid local minima such as point b, the algorithm calculates signed addition of derivatives within a specified neighborhood of each of these transition points. This weights the calculation towards large minima over the smaller local minima that occur naturally on the skull surface. If multiple large minima are found in the region of interest, the one closest to the approximate symmetric midline is chosen. Mathematically speaking, point a is found by searching for the maximum second derivative as follows:

$$x_a = \mathrm{argmax}_x [-(f(x) - f(x - w)) + (f(x + w) - f(x))] \quad (2)$$
$$= \mathrm{argmax}_x [f(x + w) + f(x - w) - 2f(x)]$$

where w is the neighborhood width.

At step 44, the falx cerebri in lower skull region is detected. The anterior bone protrusion provides the starting point for the ideal midline. A suitable end point is the falx cerebri at the other end of the skull, which is now detected from the windowed image W extracted in step 42. At step 44*a*, a threshold is applied using median. The falx cerebri appears in the window W as alight grey line against darker background matter. To help detect this lighter line, the algorithm first calculates the median grey-level value of all the pixels in W. Each pixel is then examined in turn, with all grey-level values below the median being changed to the median. After this step, only the much brighter pixels will retain their original gray levels, simplifying the edge map generated in step 44*b*. In step 44*b*, zero-crossing edge detection is performed. An initial edge map is generated using a zero crossing edge detector. This applies the Laplacian operator to W to obtain its second order derivative, then searches for points where the value passes through zero; i.e., points where the Laplacian changes sign. These are recorded, in an edge map Z: Zero crossing retains almost all possible edges regardless of sharpness or grey-level intensity value; this ensures the falx cerebri line will appear somewhere in the map, but also requires filtering of unwanted edges and objects. Step 44*c* refines the edge map using intensify and gradient. The edge map Z is refined by overlaying it with W. Specifically, the algorithm removes any points in Z whose corresponding pixels in W have a grey-level intensity value less than the 85th percentile of the intensity values across all of W. Also, the sharp edge of the falx cerebri means there is a steep grey-level intensity gradient between the pixels on the line and the pixels either side of the line. This information is incorporated by calculating the Sobel edge map S of W, which extracts edges based on steep intensity gradients. A gradient threshold is selected as a percentage of the maximum value in S; all points in S below this threshold are removed. A filtered edge map F is then constructed using only those points that appear in both Z and S. At step 44*d*, the edge map is refined using size and concentration thresholds. Even after filtering, there will still be small unconnected point clouds close to the edges in E, due to CT noise. The Hough transform in step 44*e* may try to combine these and generate inaccurate lines. This is avoided by erasing all edge segments consisting of less than 3 connected pixels. A final filtering step is performed by dividing the map into a series of vertical strips, each 10 pixels wide, and counting the number of edge points in each. After rotation, the falx cerebri in the CT scan is almost vertical; therefore, the vertical strip containing it must have a higher number of edge points. The top three strips in terms of edge points are retained, and the edge points in all other strips are removed from E. In step 44*e*, Hough Transform is used to find straight lines Hough transform is applied to E to defect candidate falx cerebri lines. This algorithm examines each pixel in the edge map and identifies straight vertical lines longer than a specified length. For each of these, it constructs a straight line equation y=mx+b, and increases the value of the corresponding bins for m and b in a two dimensional (2D) accumulator array. After all pixels are considered, the parameters of the bins with values above a certain threshold are used to construct a set of candidate falx cerebri lines. Finally, in step 44*f*, the falx cerebri line is selected. Two constraints are applied to the candidate set in order to identify the line most likely to represent the falx cerebri. First, the angle of the line to the vertical must be in a similar range to all other lines in the set. This removes outliers. Second, the line should be clustered with other lines, since multiple straight lines are likely to be detected, close to the falx cerebri. The best approximation of the falx cerebri is chosen as the longest line satisfying these two constraints.

At step 45, the detected features returned by step 44 are used to refine midline position. If both the falx cerebri and anterior protrusion are detected, the ideal midline is redefined as the straight line joining both features. However, these features may not be visible in all slices. In slices where only one is present, the symmetric exhaustive rotation search described earlier is repeated with a smaller range and smaller degree steps around whichever feature is detected. If neither feature is present, the initial approximate midline is used. Sometimes this is sufficient; however, the skull shape is complex and symmetry alone typically does not reflect the true ideal midline. This problem is addressed in step 46.

At step 46, a consistency check is made across multiple scan slices. When considering the CT scan as a whole, the system separates slices into two classes. "First class" slices are those where both the anterior protrusion and falx cerebri are detected. In "second class" slices, one or both of these features are missing; ideal midline detection in these cases may not be truly accurate. The system therefore introduces a consistency check that compares the midlines detected over consecutive slices to detect abnormalities. Initially, the "first class" slices are checked. The horizontal distance of any slice midline in this group from the group median should not exceed a specified threshold. If it does, the midline for that slice is adjusted to be the "first class" median. Next, the "second class" slices are considered. When checking a "second class" slice S, the closest "first class" slice F is located. If the distance between the midline in F and the midline in S exceeds a specified threshold, the midline of S is adjusted to match that of F. Inaccurate midline detection seldom occurs in consecutive image slices, and it is reasonable to assume that the midline should not change much across several consecutive slices of the scan.

Figure 8:
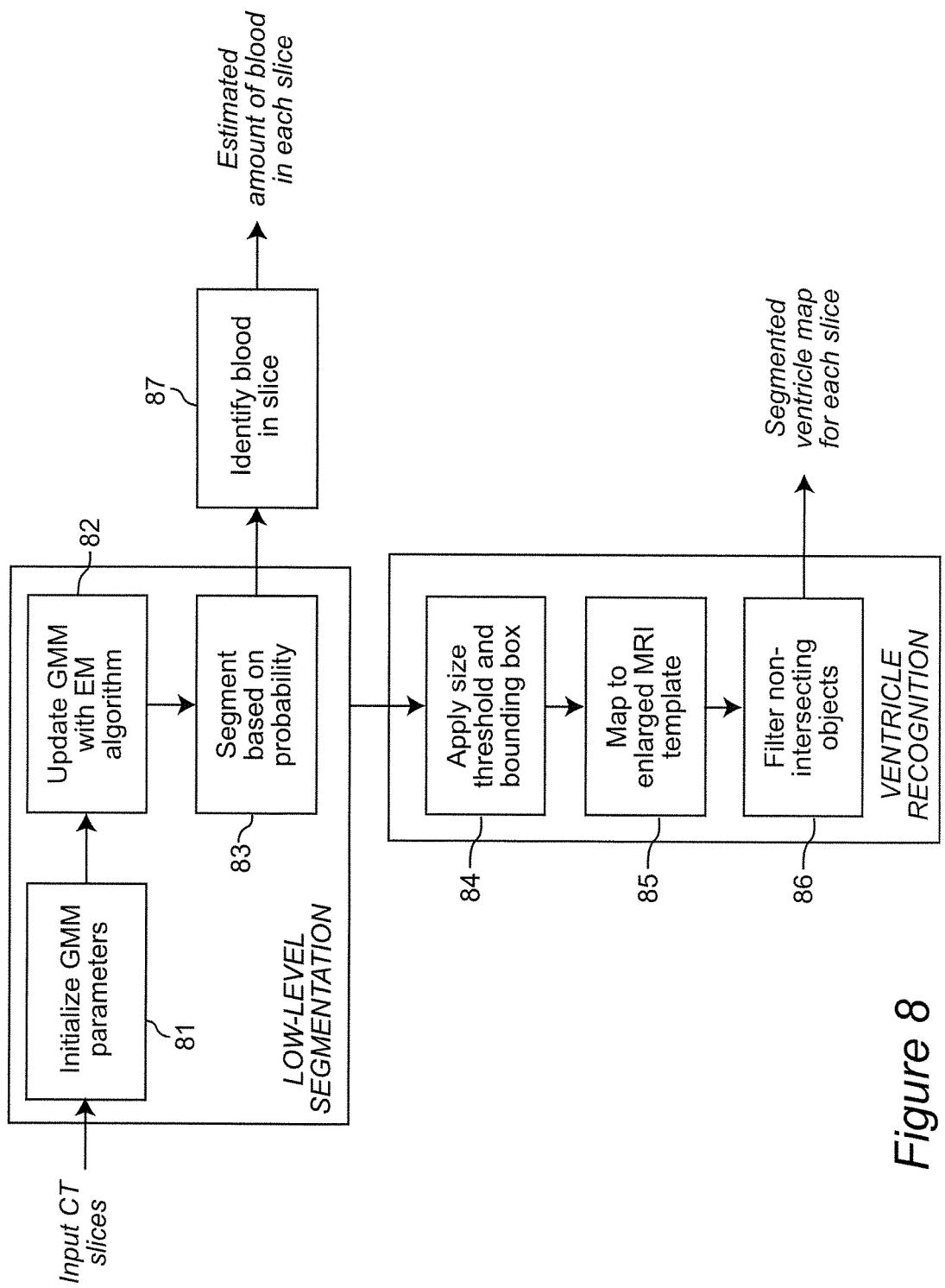
FIG. 8 is a flowchart illustrating in more detail the logic implemented by the ventricle detection and blood level estimation component shown in FIG. 3.

The step 32 in FIG. 3 is illustrated in more detail in FIG. 8. The stage input is an axial brain CT scan in the form of sequential slice image files. The stage output is a set of segmented ventricle maps and estimated blood amounts, one for each scan slice.

Prior to explanation of the flowchart steps of FIG. 8, a brief explanation of the Gaussian Mixture Model (GMM) is needed. A mixture model is a probabilistic model whose distribution is actually a convex combination of other probability density functions. In the case of a Gaussian Mixture Model (GMM), these functions are Gaussians. GMMs are currently popular in a wide variety of image segmentation applications. The most popular way of training a GMM is via Expectation-Maximization (EM). After training, the GMM is able to analyze individual image pixels and calculate the probability that they belong to a tissue class k. Each class k is represented by the regular Gaussian parameters in the grey-level intensity space (the mean and the covariance matrix). In this way, GMM offers more flexibility than a standard classifier, which simply outputs one label per pixel.

In the application of the embodiment of the invention, the GMM has the following probability distribution for each image pixel:

$$f(v_t | \Theta) = \sum_{i=1}^{m} \alpha_i f_i\left(v_t | \mu_i, \sum_i\right) \quad (3)$$

where n is the total number of Gaussian distributions in the model, $v_t$ is the feature vector of pixel t (in this case, location and grey-level intensity values) and $\Theta$ contains the model parameters. These parameters consist of $\alpha_i$, $\mu_i$ and $S_i$ for i=1, ..., n. Here, $\mu_i$ and $S_i$ are the standard parameters used to define a Gaussian (i.e., the mean and the covariance matrix), and $\alpha_i$ controls the contribution of the ith Gaussian to the model (i.e., its weight). This equation provides the probability of a pixel having the appearance parameters $v_t$.

Suppose there are k different regions to be segmented in a CT slice. To decide which region a pixel is most likely to belong to, the algorithm calculates the posterior probability for each region j:

$$p(v_t \in region_j | v_t) \quad (4)$$

Or, the probability that a pixel will belong to region j given its location and intensity value. The region with the highest probability is then chosen.

To describe the connection between the model's Gaussians and actual tissues in the CT images, a mapping is introduced between the Gaussian index and a region index, defined as π: 1, ..., n→1, ..., k (where n is the number of Gaussians and k is the number of regions). In the application of the embodiment of the invention, k=4 for four separate tissue types: bone and blood, ventricular tissue, light grey tissue, and dark grey tissue. To reduce the number of model parameters to be estimated and therefore speed up computation, it is assumed that there is no dependency between location and intensity; i.e., a region's shape is independent of its grey-level appearance. More details on the GMM method can be found in "Constrained Gaussian mixture model framework for automatic segmentation of mr brain images" (H. Greenspan, A. Ruf, and J. Goldberger, *IEEE Trans. Med. Imaging*, vol. 25, no. 9, pp. 1233-1245, 2006).

Returning again to the drawings, and more particularly to FIG. 8, the first step 81 is to initialize GMM parameters. Since the four different tissue types being modeled differ in their grey-level appearance, a simple way to initialize the GMM model is via K-means clustering. K-means is a simple and widely-used clustering algorithm, which in this case assigns pixels to the closest cluster by their grey-level values. However, due to noise in the CT slice, these cluster regions typically consist of multiple unconnected sub-regions. The algorithm therefore tests each cluster region to see if it can be represented by a single Gaussian. This Gaussian forms an ellipse in the image, so the test simply examines what percentage of the ellipse contains the tissue represented by the region. If this percentage falls below a certain threshold, the region is split into two sub-regions (again using K-means, this time based on pixel location) and the test process is repeated for these. If the percentage is above the threshold, the single Gaussian is assigned to represent the region. This top-down approach ensures every region is well represented by its Gaussian distribution, which is crucial in successful parameter estimation via the Expectation-maximization (EM) algorithm. The collected GMM parameters are the parameters for these Gaussian distributions.

At step 82, the GMM is updated with the EM algorithm. Once each parameter has an initial estimate, the EM algorithm is used to iteratively update each one. More details on the EM method can be found in "Maximum likelihood from incomplete data via the EM algorithm" (A. P. Dempster, N. M. Laird, and D. B. Rdin, *Journal of the Royal Statistical Society, Series B*, vol. 39, pp. 1-38, 1977). The detailed equations explaining how EM is used to train GMM can be found in the Greenspan paper cited above.

When a probabilistic model is dependent on hidden data, EM is ideal for estimating the best parameters. In the application of the embodiment of the invention, the hidden data consists of the true tissue membership functions for each pixel, and the observed data are the pixel feature vectors (location and grey-level values). The best model parameters are those that maximize the likelihood of the observed data; to find these, EM attempts to maximize the likelihood of the complete data (i.e. the observed data and hidden data combined). As a basic intuitive description, EM consists of two stages: expectation (E) step and maximization (M) step.

E-step: Estimate the hidden data (the pixel membership functions) using the observed pixel feature vectors and the current estimate $\theta_z$ of the model parameters $\Theta$.

M-step: Using the new estimate of the hidden and with the observed pixel feature vectors, estimate the most likely parameters $\theta_{(z+1)}$.

This process is repeated iteratively until the estimate converges, i.e., there is no significant change between iterations—giving the most likely estimate $\theta_m$ of $\Theta$.

At step 83, a segmentation is made based on probability. After the GMM parameters are estimated, the posterior parameters given in equation 4 are calculated using the Bayes rule.

$$p(v_t \in region_j \mid v_t) = \frac{p(v_t \in region_j \mid v_t)}{p(v_t)} \propto p(v_t, region_j)$$

$$p(v_t, region_j) = \sum_{i \in \pi^{-1}(j)} \alpha_i f_i\left(v_i \mid \mu_i, \sum_i\right) \quad j = 1, \ldots, k$$

where $\pi^{-1I}$ (j) returns all Gaussian indexes belonging to region j. The most probable tissue label $l_t$ for the pixel with feature vector $v_t$, is:

$$l_t = \arg\max_{j \in 1, \ldots, k} p(v_t, region_j)$$

This returns a set of candidate ventricle objects (clusters of connected pixels identified as ventricular tissue.

Step 84 applies a size threshold and a bounding box. Though it deals well with the noise present in CT images, the low-level GMM segmentation step is based only on each pixel's grey-level value and location, and does not use any anatomical knowledge. Therefore, some objects it labels as ventricular tissue are not actually part of the ventricles. Step 84 first applies a size threshold to each of the candidate ventricle objects, removing those with areas below a specified threshold (as these are likely to be image artifacts and noise). Two bounding boxes are then created: one large and one small, both centered in the middle area of the skull, where the lateral and third ventricles are likely to be located. If a candidate object extends beyond the edge of the large bounding box, or has no part inside the small bounding box, it is removed from the candidate set. This filtering step narrows down the candidate range in preparation for template matching.

Step 85 maps to an enlarged MRI template. The bounding box step removes non-ventricular objects close to the edge of the skull, but some are too close to the true ventricle objects. To remove these, template matching is performed using a set of template images generated from a brain MRI scan (which offers better definition of soft tissue). The shape and location of the lateral ventricles changes across the slices of a CT scan; if the position of the current slice in the sequence is known, more precise constraints can be used. The embodiment of the invention calculates this based on the resolution of the direction perpendicular to the axial plane (the z-direction), then compares the location and shape of the candidate ventricle objects to the ventricles in the appropriate template image. Note that the template set was generated manually, with ventricles being enlarged in size to deal with variation between patients and shift in ventricle position caused by increased ICP.

Step 86 filters non-intersecting objects. The CT slice and appropriate template are aligned. Any candidate ventricle objects that intersect with the ventricles in the template are accepted as true ventricle objects. These objects are returned in a segmented ventricle map to be used in calculating the ideal midline.

Step 87 identifies blood in the CT slice. This is a separate step performed after step 83, using the results of low level segmentation via GMM. GMM identifies some of the pixels in the CT slice image as bone and blood tissue, which share very similar grey-level values. The only bone tissue in the slice is the skull wall, which was identified in step 41a in FIG. 4. The amount of blood in the slice is therefore calculated by subtracting the skull wall pixels from the set of bone and blood pixels returned by GMM.

Figure 9:
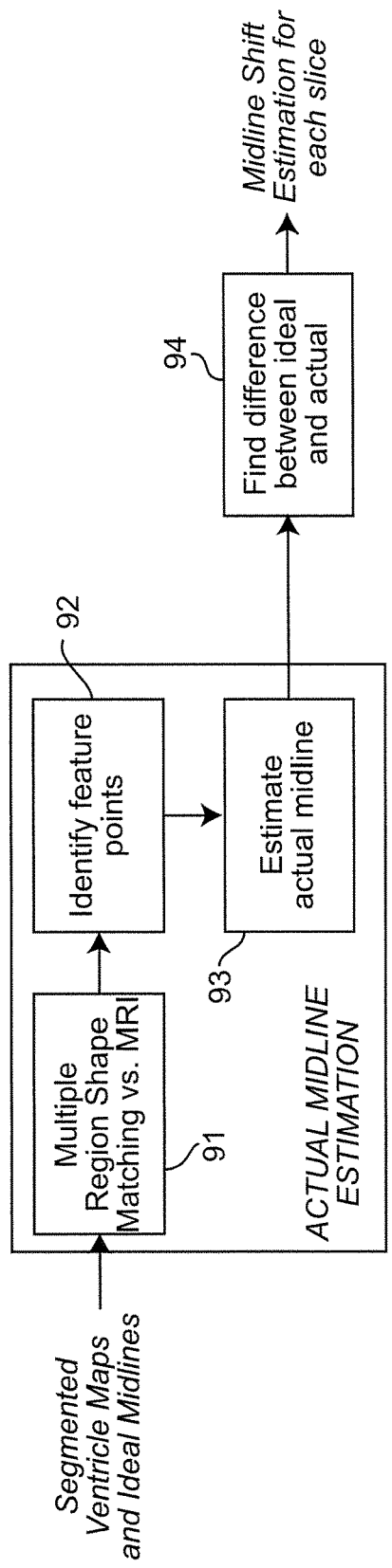
FIG. 9 is a flowchart illustrating in more detail the logic implemented by the process of the actual midline estimation and calculating shift from the ideal midline component shown in FIG. 3.

FIG. 9 illustrates in detail the process of estimation of the actual midline and shift calculation, shown at step 33 in FIG. 3. The input to this stage is the set of segmented ventricle maps calculated in the previous stage, and the output is a quantitative estimation of midline shift in each slice.

At step 91, multiple regions shape matching is performed against an MRI. The set of templates used to filter the candidate ventricle objects in step 32 of FIG. 3 was generated from an MRI brain scan. However, MRI scans typically have a higher slice density than CT scans; i.e., they contain more slice images across the same structure. A multiple regions shape matching algorithm (MRSM) is proposed to deal with the challenge in finding the MRI template that best matches a given segmented ventricle map S as well as the actual midline estimation.

Each MRI template $M_k$ is compared with S in turn; these are termed "shapes". Control points on the edge of every object are used to match objects from one shape to objects in another. In $M_k$ and S, these points are sampled as a fixed percentage of the detected object's edge points. The cost of matching a control point $p_i$ in S with a control point $q_j$ in $M_k$ is defined as:

$$C(p_i, q_i) = \frac{1}{2} \sum_{k=1}^{K} \frac{[h_i(k) - h_j(k)]^2}{h_i(k) + h_j(k)}$$

where $h_i(k)$ and $h_j(k)$ are the K-bin normalized histograms at $p_i$ and $q_j$. The best match for each control point in S and $M_k$ aims to minimize the sum of all matched points between the two shapes. Typical shape matching would use the total shape match cost between S and $M_k$ as a measurement of dissimilarity of shapes. However, this is not suitable for the application of the embodiment of the invention, as we are dealing with pathological cases. For example, if the two lateral ventricles have undergone shift, the distance between them may be much greater than in the template. This changes the histogram of each control point and causes incorrect matches. Also, shift may cause one ventricle to shrink and the other to expand. If the control points on the edge of each shape are sampled uniformly, the smaller ventricle will have fewer control points than the larger; however, the ventricles in the template have roughly the same number of points on both sides. Again, this will lead to unreliable matches. To address this, the system employs a multiple regions shape matching scheme. The shape-matching process above is applied first, to generate a set of corresponding point pairs that reflects an approximate correspondence between the objects in S and $M_k$. For the next stage, point pairs with match cost below the 30th percentile are retained as the reliable corresponding points.

Each object $A_i$ in S is now considered in turn. The average number $n_i$ of control points matches between $A_i$ and $M_k$ is calculated; in other words, the algorithm counts how many control points on $A_i$ match control points on each object in $M_k$, sums the results, and divides by the total number of objects in $M_k$. Any object $B_j$ in $M_k$ that shares more than 0.5 $n_i$ matched points with $A_i$ is recorded as being "related" to $A_i$. The same process is repeated for each object $B_j$ in $M_k$, considering all objects in S. Objects that are related directly or indirectly (via other objects) form a set of matched objects. Each of these sets contains a subset of objects in S and a subset of objects in $M_k$.

Figure 10:
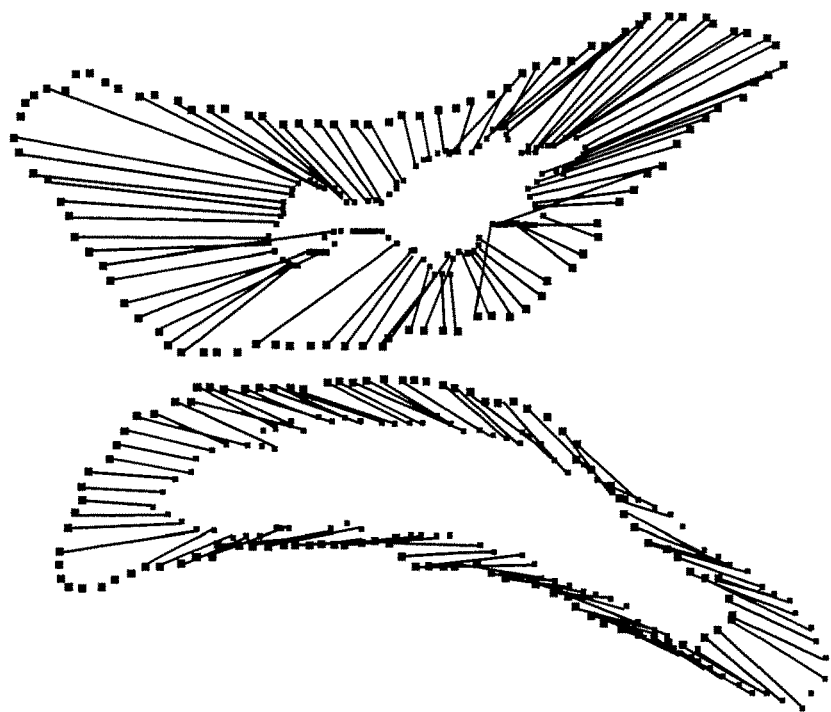
FIG. 10 is a graphical illustration explaining the advantages of MRSM when a segmented ventricle is much smaller and with different distance between regions in pathological cases than the template ventricle.
Figure 10:
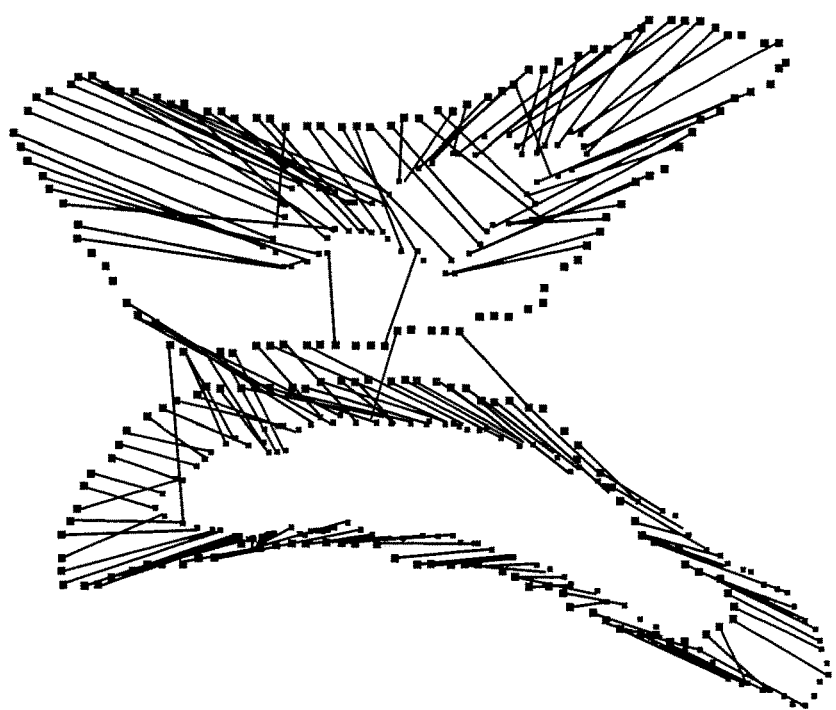

New control points are placed on the edge of the objects in each matched set by resampling. This solves the problem described earlier when one lateral ventricle is much smaller than the other. FIG. 10 provides an example to explain the advantages of MRSM when a segmented ventricle is much smaller than the template ventricle. Standard shape-matching (seen on the left) using shape context (see, S. Belongie, J. Malik, and J. Puzicha, "Shape Matching and Object Recognition Using Shape Contexts", *IEEE Trans. on Pattern Analysis and Machine Intelligence,* 24(25):509-521, April 2002) creates incorrect correspondences (lines crossing between ventricles) and leads to inaccurate cost calculations. The results on the right are from MRSM, where each ventricle is correctly matched with its template. MRSM ensures that an equal number of control points are placed around the edge of both objects, improving match results.

The total cost of matching slice S with a template $M_k$ is calculated by a weighted average among the costs of all the matched sets based on the size of objects. This process is carried out over all templates k=1, ..., n; the best template for S is selected as the one with the lowest total matching cost.

Steps 92 and 93 identify inner edge feature points and estimate actual midline. After shape-matching, detection of the left side and right side of lateral or third ventricles is complete. The actual midline is now calculated as the line best dividing them in the ventricle map S. The feature points used to calculate the midline on the MRI templates were placed manually. The feature points on segmented ventricle are labeled by corresponding features points on the template. Take the lateral ventricle for example. Those that were placed on the inner edge of the left lateral ventricles were assigned a label L, and those on the inner edge of the right lateral ventricle a label R. When the feature points in the best template are matched to the corresponding points in the segmented ventricle map S, these labels propagate. Therefore, after shape matching, this propagation has identified which feature points in S belong to the inner edges of each ventricle. The system calculates the mean x-coordinate of the control points on the inner edge of each ventricle in turn, then averages the two values to calculate the x-coordinate of the actual midline.

Step 94 finds the difference between ideal and actual midlines After the actual midline has been located, estimating horizontal shift s is straightforward:

$$s = |x_i - x_a|$$

where $x_i$ is the ideal midline and $x_a$ is the estimated actual midline.

The process in steps 91 to 94 is repeated for each segmented ventricle map in turn. This stage therefore returns a set of estimated midline shift values (one for each input slice).

Figure 11:
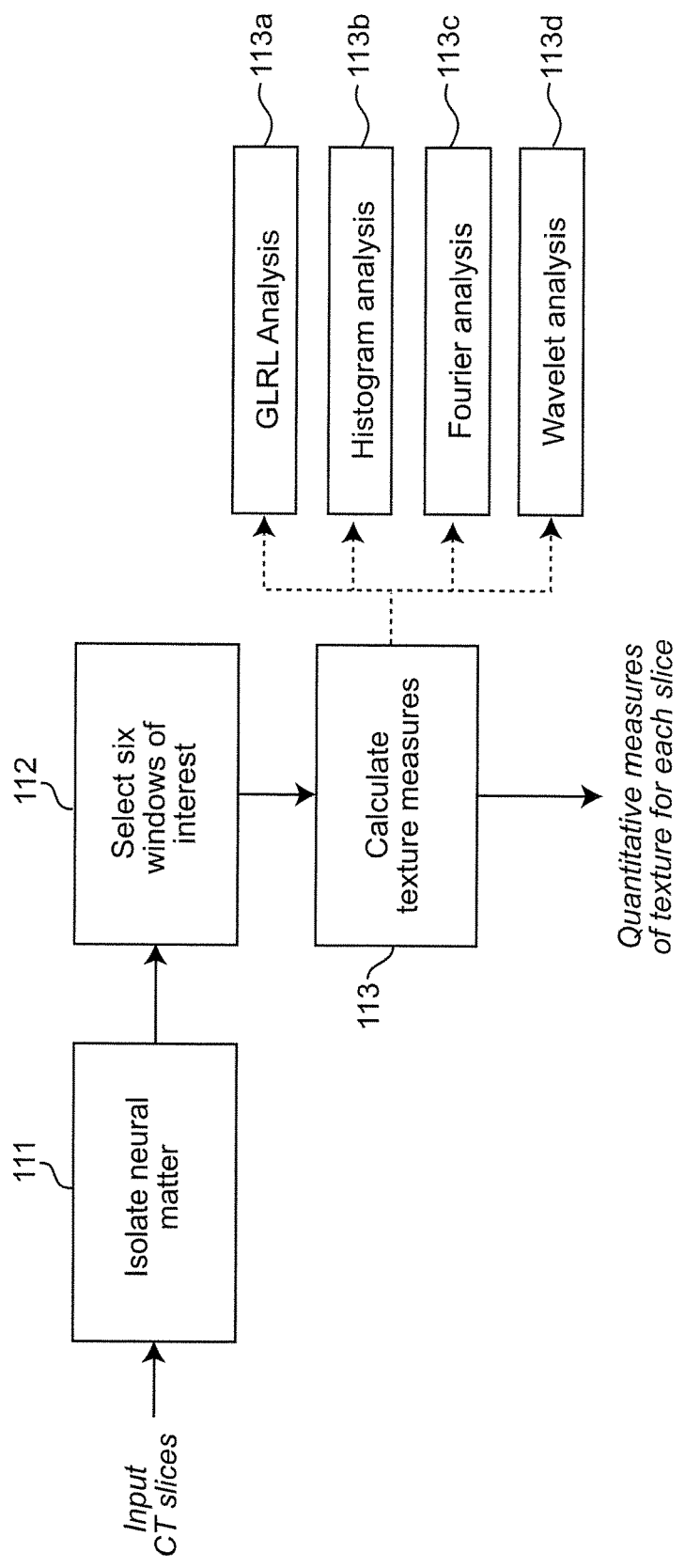
FIG. 11 is a flowchart illustrating the logic of the texture analysis component shown in FIG. 2.

FIG. 11 illustrates in more detail the texture analysis process 22 shown in FIG. 2. The input to this stage is a set of slice images from a CT brain scan: The output is a set of quantitative measures of texture for each slice.

The first step 111 is to isolate neural matter. The skull wall was identified in step 41a shown in FIG. 4, and extracted as a bone mask. This is subtracted from the CT scan slice to create an image containing only the brain tissue to be used for texture analysis.

Figure 12:
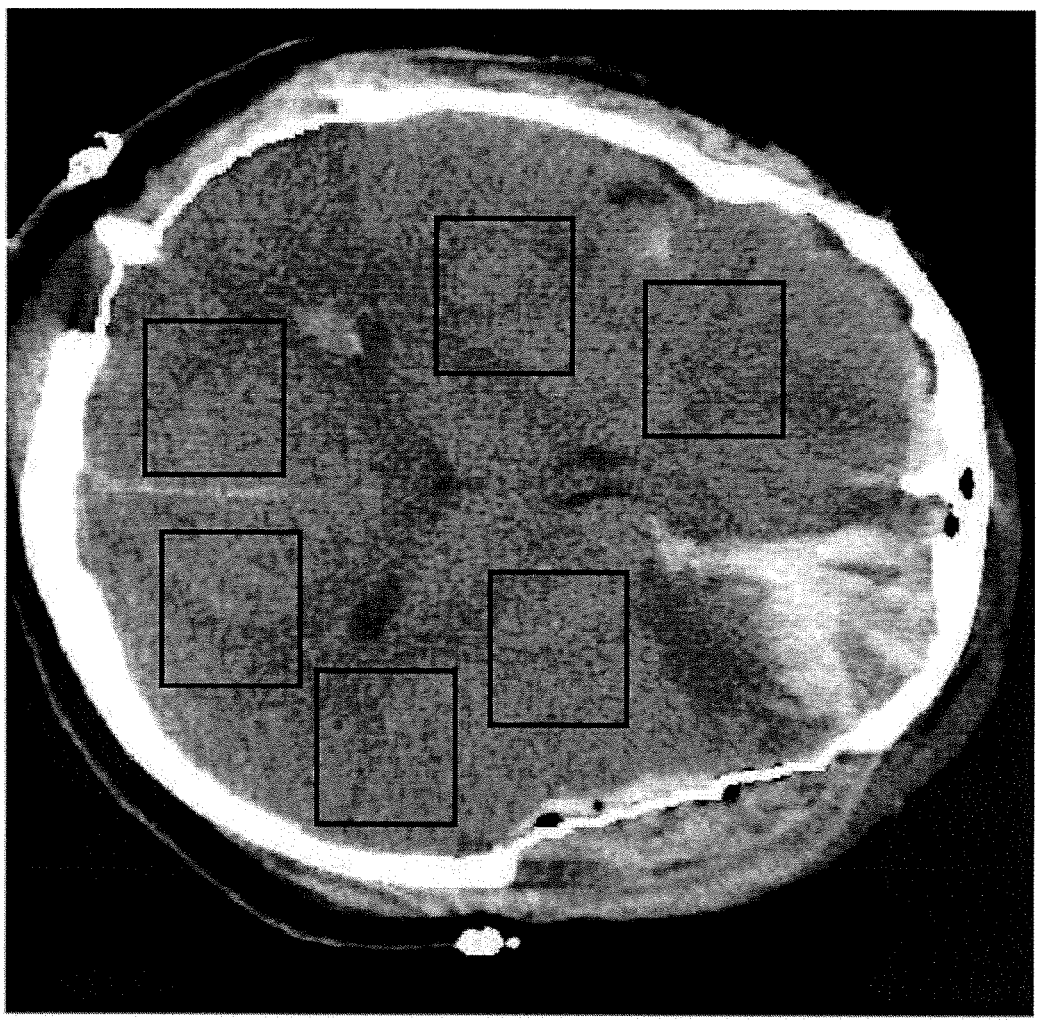
FIG. 12 is an image of a CT slice showing locations of analyzed windows.

At step 112, six windows of interest are selected. Six rectangular windows are extracted from each of the five selected CT slices. Since the position of the ventricles and blood are known after step 111, and the pixels representing bone have already been zeroed out, these windows can be automatically selected to contain primarily dark grey and light grey tissue. FIG. 12 illustrates example windows. Each window is processed separately, with a total of 48 texture features being extracted using five methods: Grey Level Run Length Matrix (GLRLM), Histogram analysis, Fourier Transform, Discrete Wavelet Packet Transform (DWPT), and Dual Tree Complex Wavelet Transform (DT-CWT). This offers a very rich description of tissue texture with little increase in computational time and no negative impact on ICP prediction (since feature selection is performed in step 27, shown in FIG. 2 and described in more detail with reference to FIG. 14). Furthermore, extraction of these features allows the system to be adapted to other analysis tasks, such as detecting and quantifying diffused blood in brain tissue.

At step 113 texture measures are calculated. The five texture extraction methods are as follows: GLRL analysis, step 113a; histogram analysis, step 113b; Fourier analysis, step 113c; and wavelet analysis, step 113d. These are described in more detail below.

At step 113a, GLRL analysis, a grey-level run (GLR) can be considered a set of consecutive collinear pixels in an image which share the same grey level value. GLRs are identified by their direction, length and grey-level value, and are assembled into run-length matrices which characterize texture elements. Element P(i, j) of a run-length matrix P reflects the number of runs j of pixels with gray level value i in the specified direction for the matrix. Four directions are examined in this embodiment (0, 45, 90 and 135 degrees), generating four matrices. Each of these is used to calculate eleven different texture features: Short Run Emphasis (SRE), Long Run Emphasis (LRE), Grey Level Nonunifomiity (GLN), Run Length Nonunifomiity (RLN), Run Percentage (RP), Low Gray-Level Run Emphasis (LGRE), High Gray-Level Run Emphasis (HGRE), Short Run Low Gray-Level Emphasis (SRLGE), Short Run High Gray-Level Emphasis (SRHGE), Long Run Low Gray-Level Emphasis (LRLGE), and Long Run High Gray-Level Emphasis (LRHGR). These provide a statistical characterization of image texture based on both gray-level and run-length that can be used as input to the classification process. Their mathematical formulations can be found in "Texture information in run-length matrices" (X. Tang, *IEEE Trans. on Image Processing,* 7(11):1602-1609, 1998).

At step 113b, histogram analysis, four features are obtained from the histogram for each window: average intensity level, average contrast, smoothness and entropy. The first two measures are respectively defined as the histogram's mean and standard deviation. A measure of smoothness is provided by:

$$R = 1 - \frac{1}{1+\sigma^2}$$

where σ is the standard deviation of the histogram. A value approaching 0 indicates low variation in pixel value intensity (i.e., smooth texture), while a value approaching 1 shows much higher variation (i.e., rough texture). The final feature, histogram entropy, reflects the randomness of intensity values.

At step 113c, Fourier analysis, the two dimensional (2D) Fast Fourier Transform (FFT) is applied to each window. FFT is a computationally efficient version of the Discrete Fourier Transform (DFT) which is typically used to translate a time-domain function into the frequency domain. In the case of the window image of the embodiment of the invention, the 2D FFT is used, which applies FFT to each row in the window, replaces the row with the resulting Fourier transform, then repeats the same process with each column. More formally, if each row or column is considered as a sequence of values $x_0, \ldots, x_{N-1}$, FFT generates a sequence of N complex frequency components $X_0, \ldots, X_{N-1}$ as follows:

$$X_k = \sum_{n=9}^{N-1} x_n e^{\frac{2\pi i}{N} kn} \text{ for } k = 0, \ldots, N-1$$

The maximum, minimum, average and median of the frequency components are calculated as texture features, along with the component corresponding to the median value of the absolute value.

Step 113d, wavelet analysis, actually incorporates two separate measures: Discrete Wavelet Packet Transform (DWPT) and Dual Tree Complex Wavelet Transform (DT-CWT), which are extensions of Discrete Wavelet Transform (DWT). The standard Discrete Wavelet Transform (DWT) decomposes a signal by passing it through a series of filters at consecutive levels of decomposition. At each level i, a high-pass and low-pass filter are used to extract detail and approximation coefficients from the signal passed by the previous level. The detail coefficients are stored, and the approximation coefficient is then passed on to the subsequent level (i+1). In image processing, the 2D DWT is used, where the image is regarded as a series of one dimensional (1D) row signals and as a series of 1D column signals. The 1D DWT is calculated for each row, and the N rows of resulting values are used to form a matrix $X_v$. The same is repeated for columns to form a matrix $X_h$. This decomposition process is repeated on $X_v$ and $X_h$, creating four final output matrices of detail coefficients: $X_{hh}$, $X_{vv}$, $X_{hv}$, and $X_{vh}$. These coefficients characterize the texture of the image. More information on 2D DWT can be found in *Biomedical Signal and Image Processing* (K. Najarian and R. Splinter, The CRC Press, ISBN: 0849320992, 2005). This multi-resolution analysis is highly effective in detecting localized texture patterns.

The Discrete Wavelet Packet Transform (DWPT) used in this embodiment of the invention extends DWT by also decomposing the detail coefficients at each level, rather than just the approximation coefficient. Though this incurs a higher computational cost, it provides a richer representation of texture which is valuable to the task in this study. More details can be found in "Rotation and scale invariant texture features using discrete wavelet packet transform" (R. Manthalkar, P. K. Biswas and B. N. Chatterji, *Pattern Recognition Letters*, 24(14):2455-2462, 2003).

Complex Wavelet Transform (CWT) is an extension to standard DWT which offers better performance in processing images than 2D WT. At each level of standard 2D DWT, the image is sub-sampled by factor 2 in each direction, creating four smaller sub-images for the next level of decomposition. As the image size decreases, decomposition becomes increasingly susceptible to shift and aliasing. CWT combines DWT with Fourier Transform (FT) by using a complex-valued wavelet and scaling function. One specific advantage of CWT for our application is that it maintains directionality, improving detection of texture ridges. The dual-tree CWT (DT-CWT) employed in this study is an implementation of CWT which creates two separate DWT decompositions in parallel. This redundancy provides shift invariance at relatively low computational cost. More details can be found in "Complex wavelets for shift invariant analysis and filtering of signals" (N. G. Kingsbury, *Journal of Applied and Computational Harmonic Analysis*, 10(3): 234-253, May 2001).

Figure 13:
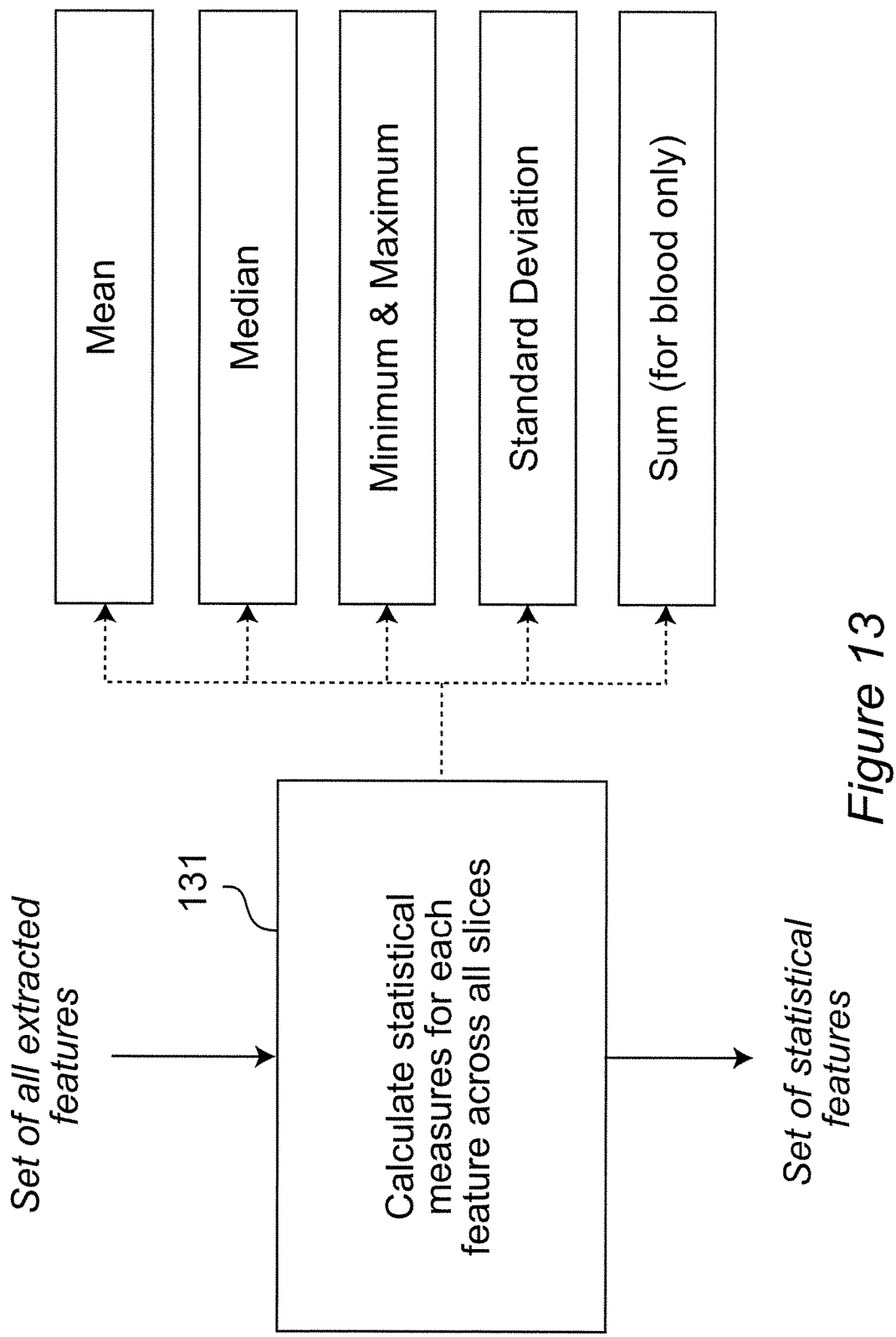
FIG. 13 is a flowchart illustrating the logic of the feature aggregation component shown in FIG. 2.

The process of feature aggregation and extraction, step 25 in FIG. 2 and step 113 shown in FIG. 11, is described in more detail with reference to FIG. 13. This stage of the system collects the features extracted from each slice of the CT scan and uses them to calculate a new set of statistical measures to be used in ICP prediction. The input to this stage is the set of raw features extracted from the scan slices. The output is a set of statistical features calculated across the entire scan.

At step 131, the statistical measures are calculated for each feature across all scan slices. Since steps 21 and 22 (FIG. 2) are applied to each individual slice, the output set of features, including texture, midline shift, and amount of blood, is very large. This stage considers each feature in turn, aggregates its values over the scan, and calculates several statistical measures. For a given feature f, these are min(f), max(f), $\mu$(f), $\sigma$(f), and median(f). In other words, the minimum value, the maximum value, the mean, the standard deviation, and the middle value when all values are sorted in ascending order. For blood amount, $\Sigma$(f) is also calculated (the total amount of blood detected across all the slices).

Figure 14:
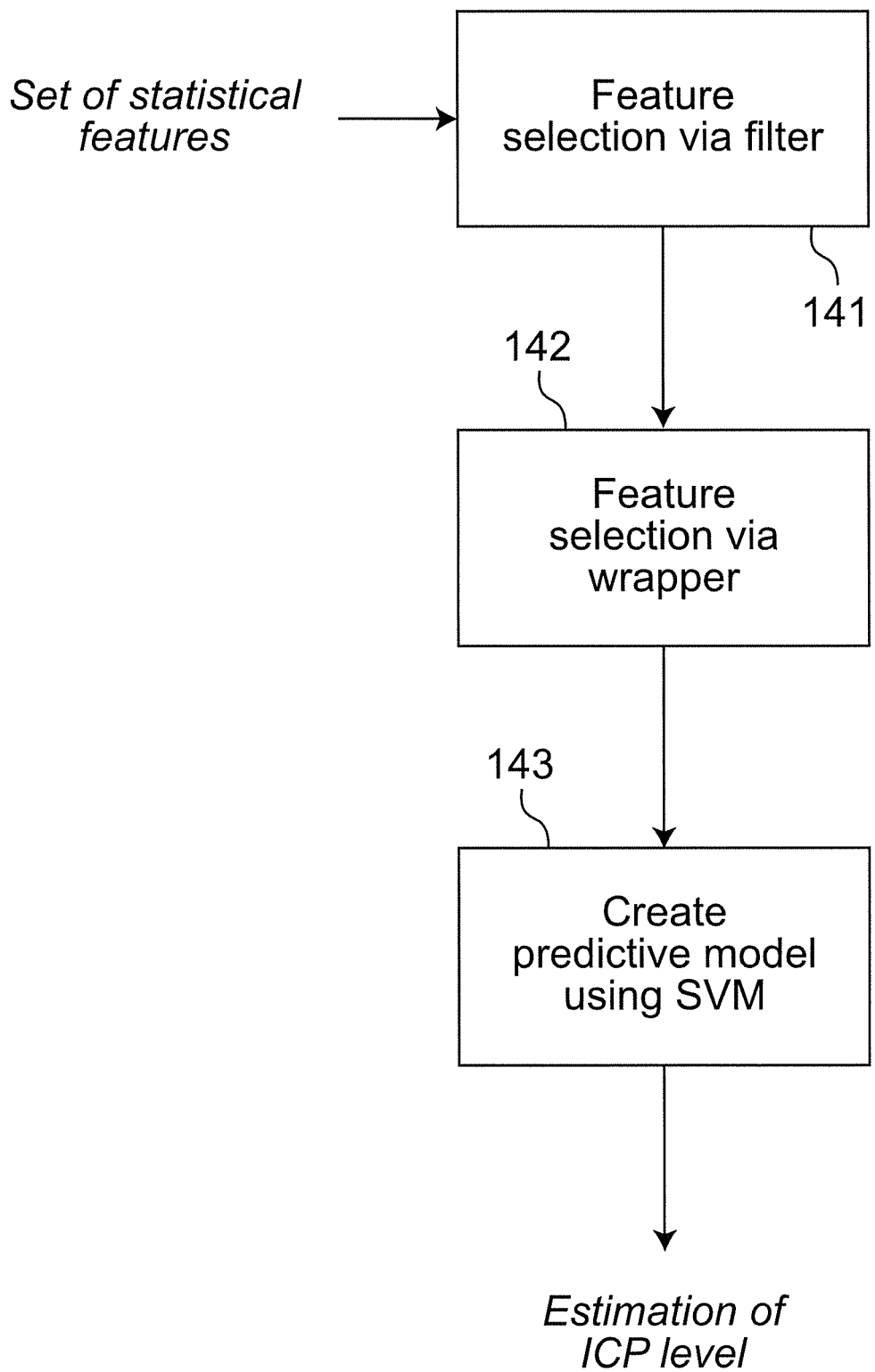
FIG. 14 is a flow chart illustrating the logic of the SVM prediction component shown in FIG. 2.

The process of machine learning for ICP prediction, step 27 in FIG. 2, is shown in more detail in FIG. 14. This stage generates a predictive model for ICP estimation using the feature set generated in feature aggregation and extraction, step 25 in FIG. 2, and described in more detail with reference to FIG. 11. Note that this stage requires prior training of the model on a dataset of prior patients with known ICP values, using the Support Vector Machine (SVM) algorithm. After training and validation, this model is then ready to deploy in a real-world environment for use in estimating the condition of a new patient in real-time based on their CT scan. The input to this stage is a set of statistical features calculated from the raw scan feature set. The output is an estimation of ICP level (or, if training, a predictive model of ICP severity)

At steps 141 and 142, feature selection is done via filter and wrapper. Due to the number of features extracted from the CT scan, feature selection must be performed to remove those which are redundant or irrelevant for the current predictive task. This is done via a two-step filter-wrapper approach. In the first stage, the ReliefF algorithm is used to rank the features in terms of their significance. The top 50 are then passed to the second stage, which uses SVM with 10-fold cross-validation to test multiple subsets of the input features, and selects the one that offers the best classification accuracy on the training dataset. This feature subset is used to construct the model. For more information on ReliefF, see "An adaptation of relief for attribute estimation in regression" (Marko Robnik-Sikonja and Igor Kononenko, Proceedings of the Fourteenth International Conference on Machine Learning, pp. 296-304, 1997).

At step 143, a predictive model is created using Support Vector Machine (SVM). SVM is a machine learning technique used primarily for classification. It is a supervised method, meaning that, given a training set of example cases labeled with categories, it constructs a model that predicts the most suitable category for a new, unlabeled example. In a mathematical sense, SVM constructs a hyperplane in high-dimensional space which best preserves separation between the various categories (classes). Each of the examples is treated as a data-point in this high-dimensional space, so the optimal hyperplane can be considered as the one that divides the classes by as wide a gap as possible. Essentially, it is based on the distance between data-points. Since SVM performs well on complex data (where many features are used for prediction), it has been successfully used in solving many real world problems such as protein analysis, cancer data classification, and hand-writing recognition.

The standard SVM model groups patients into two classes: severe ICP (>15) and non-severe (≤15). This was agreed on after discussion with trauma physicians. However, it is possible for the model to be re-trained with a larger number of classes, depending on the quantity of prior cases available.

The initial training stage is performed on a dataset of prior cases containing CT scans and ICP values for a large number of patients, and outputs a predictive model that can be deployed in a clinical environment. After this, the model is integrated into a software program for use by physicians. This stage then takes as input a CT scan set from a new patient, and outputs an estimate their current level of ICP. Note that the model generation process can be easily repeated as new patients become available to generate an updated predictive model, which can simply be swapped in to replace the existing one. As stated above, the number of classes could also be increased during this process.

The midline shift measurement as implemented by an embodiment of the invention can be adapted to Magnetic Resonance Imaging (MRI) data with the change on the detection of the bone protrusion and falx cerebri. For the bone protrusion, the threshold should be close to dark because the bone region in MRI is in low intensity range. The thresholding for falx cerebri should also change to represent the intensity level in MRI because the falx cerebri also becomes dark in MRI. The segmentation of ventricles from MRI using Gaussian Mixture Model (GMM) (see H. Greesnpan et al., ibid.) and the actual midline estimation using shape matching can be used directly.

While the invention has been described in terms of a single preferred embodiment, those skilled in the art will recognize that the invention can be practiced with modification within the spirit and scope of the appended claims.

Having thus described our invention, what we claim as new and desire to secure by Letters Patent is as follows:

1. A computer automated method for the measurement of brain injury indices, comprising:
   receiving, at a computer, computed images of a patient's brain including a ventricle system;
   processing the computed images of the patient's brain to detect anatomical features in bones and tissue specific to the patient's brain;
   detecting an ideal midline of the patient's brain based on the detected anatomical features in bones and tissues specific to the patient's brain;
   segmenting out ventricles in the computed images of the patient's brain by computer analysis of ventricle system deformation in the computed images;
   estimating an actual midline of the patient's brain by matching a shape of a ventricle in the computed images of the patient's brain with the ventricle system segmented out to a ventricle template set;
   calculating a shift or deformation based on the ideal midline and the actual midline to provide an indication of the midline deformation around the ventricle system;
   receiving patient demographics information and/or injury information;
   generating, from the calculated shift or deformation indicating the midline deformation and from the patient demographics information and/or injury information, an indication of intracranial pressure (ICP) severity classification; and
   displaying the indication of intracranial pressure severity classification.

2. The computer automated method according to claim 1, wherein the detecting detects a protrusion in an anterior part of bone and falx cerebri in a posterior region of tissue of the patient's brain using prior knowledge to approximately identify regions of those structures.

3. The computer automated method according to claim 1, wherein the segmenting comprises:
   performing an initial low-level segmentation; and
   performing a subsequent high-level segmentation using anatomical knowledge to filter a candidate ventricle set to detect true ventricle objects.

4. The computer automated method according to claim 3, wherein the anatomical knowledge used in performing a subsequent high-level segmentation is a magnetic resonance image (MRI) ventricle template which is used for computer estimation of regions for each ventricle, wherein the MRI ventricle template is a template configured for use with multiple patients, with multiple states of brain injuries or no brain injuries.

5. The computer automated method according to claim 4, wherein the matching is performed to select a corresponding MRI slice from an MRI ventricle template set, and
   to detect feature points for estimating the actual midline.

6. The computer automated method according to claim 3, wherein the performing an initial low-level segmentation comprises identifying blood in a CT slice to provide an estimate of amount of blood in each CT slice.

7. The computer automated method according to claim 3, wherein the segmenting comprises:
   performing the initial low-level segmentation using a Gaussian Mixture Model (GMM) via Expectation-Maximization (EM) training.

8. The computer automated method according to claim 1, wherein the computed images of a patient's brain which are input to a computer are computed tomography (CT) images.

9. The computer automated method according to claim 1, further comprising performing texture analysis of the computed images by computer analysis, the results of the texture analysis being used for ICP prediction.

10. The computer automated method according to claim 9, wherein the performing texture analysis comprises:
    isolating neural matter from CT scan images; and
    calculating with a computer texture measures using one or more analysis techniques selected from the group consisting of Grey Level Run Length (GLRL) analysis, histogram analysis, Fourier analysis, and Discrete Wavelet Packet Transform (DWPT) analysis.

11. The computer automated method according to claim 9, further including:
    aggregating, by computer, features computed from midline shift and texture analysis;
    selecting, by computer, features from among aggregated features; and
    building, by computer, an ICP model to determine ICP severity classification.

12. The computer automated method according to claim 11, further comprising receiving patient demographics and injury information and using in aggregating the features.

13. The computer automated method according to claim 12, wherein building the ICP model is preceded by a computer implemented machine learning method based on aggregated features including computed midline shift, brain tissue texture features, volume of blood accumulated in the brain, patient demographics, injury information, and features extracted from physiological signals to train a machine learning method to predict ICP, likelihood of success of a particular treatment, and the need and/or dosage of particular drugs.

14. The computer automated method according to claim 13, wherein the computer implemented machine learning method is a Support Vector Machine (SVM) algorithm.

15. The computer automated method according to claim 1, further comprising:
receiving, in addition to patient demographics information and/or injury information, brain tissue texture features; and
generating, from the calculated shift or deformation indicating the midline deformation and from the patient demographics information and/or injury information and the brain tissue texture features, the indication of intracranial pressure (ICP) severity classification.

16. An automated decision support system for the measurement of brain injury indices using computed images of a patient's brain, the system comprising:
a computer system configured to
receive computed images of a patient's brain,
processing the computed images of the patient's brain to detect anatomical features in bones and tissue specific to the patient's brain,
detect an ideal midline of the patient's brain based on the detected anatomical features in bones and tissues specific to the patient's brain,
segment out ventricles in the computed images of the patient's brain by computer analysis of ventricle system deformation,
estimate an actual midline of the patient's brain by matching a shape of a ventricle in the computed images of the patient's brain with the ventricles segmented out to a ventricle template set,
calculate a shift or deformation based on the ideal midline of the detecting step and the actual midline of the estimating step to provide an indication of the midline deformation around the ventricle system,
receive patient demographics information and/or injury information; and
generate, from the calculated shift or deformation indicating the midline deformation and from the patient demographics information and/or injury information, an intracranial pressure (ICP) severity classification, and
a display system connected to the computer system configured to display an indication of the intracranial pressure (ICP) severity classification.

17. The automated decision support system according to claim 16, wherein the computer system is configured to detect the ideal midline by detecting a protrusion in an anterior part of bone and falx cerebri in a posterior region of tissue of the patient's brain using prior knowledge to approximately identify regions of those structures.

18. The automated decision support system according to claim 17, wherein the computer system is configured to segment out the ventricles by
performing an initial low-level segmentation, and
performing a subsequent high-level segmentation using anatomical knowledge to filter a candidate ventricle set to detect true ventricle objects.

19. The automated decision support system according to claim 18, wherein the anatomical knowledge used in performing the subsequent high-level segmentation is a magnetic resonance image (MRI) ventricle template which is used for computer estimation of regions for each ventricle, wherein the MRI ventricle template is a template configured for use with multiple patients, with multiple states of brain injuries or no brain injuries.

20. The automated decision support system according to claim 19, wherein the matching is performed to select a corresponding MRI slice from an MRI ventricle template set, and
to detect feature points for midline estimating the actual midline.

21. The automated decision support system according to claim 19, wherein the computer system is configured to segment out the ventricles by
performing the initial low-level segmentation using a Gaussian Mixture Model (GMM) via Expectation-Maximization (EM) training.

22. The automated decision support system according to claim 18, wherein performing the initial low-level segmentation comprises identifying blood in a CT slice to provide a computer estimate of amount of blood in each CT slice.

23. The automated decision support system according to claim 16, wherein the computed images of a patient's brain which are received by the computer are computed tomography (CT) images.

24. The automated decision support system according to claim 16, wherein the computer system is further configured to perform a texture analysis of the computed images, the results of the texture analysis being used by the computer system for ICP prediction.

25. The automated decision support system according to claim 24, wherein texture analysis comprises
isolating neural matter from images, and
calculating texture measures using one or more analysis techniques selected from the group consisting of Grey Level Run Length (GLRL) analysis, histogram analysis, Fourier analysis, and Discrete Wavelet Packet Transform (DWPT) analysis.

26. The automated decision support system according to claim 24, wherein the computer system is further configured to
aggregate features computed from midline shift and texture analysis,
select features from among aggregated features, and
build an ICP model to determine ICP severity classification.

27. The automated decision support system according to claim 26, wherein the computer system is further configured to aggregate patient demographics and injury information with computed midline shift and computed texture analysis features.

28. The automated decision support system according to claim 27, wherein the computer system implements a machine learning method based on aggregated features including computed midline shift, brain tissue texture features, volume of blood accumulated in the brain, patient demographics, injury information, and features extracted from physiological signals to train a machine learning method to predict ICP, likelihood of success of a particular treatment, and the need and/or dosage of particular drugs.

29. The automated decision support system according to claim 28, wherein the computer implemented machine learning method is a Support Vector Machine (SVM) algorithm.

30. The automated decision support system according to claim 16, wherein the computer system is configured to
receive, in addition to patient demographics information and/or injury information, brain tissue texture features, and
generate, from the calculated shift or deformation indicating the midline deformation and from the patient demographics information and/or injury information and the brain tissue texture features, the indication of intracranial pressure (ICP) severity classification.

* * * * *